(12) United States Patent
Park et al.

(10) Patent No.: US 11,529,507 B2
(45) Date of Patent: Dec. 20, 2022

(54) INTRAVENOUS PRIMING CAP

(71) Applicant: CareFusion 303, Inc., San Diego, CA (US)

(72) Inventors: Soon Park, Cypress, CA (US); Siddarth K. Shevgoor, Mission Viejo, CA (US); Peter Ma, Shanghai (CN); Jiagui Li, Shanghai (CN)

(73) Assignee: CareFusion 303, Inc., San Diego, CA (US)

( * ) Notice: Subject to any disclaimer, the term of this patent is extended or adjusted under 35 U.S.C. 154(b) by 74 days.

(21) Appl. No.: 16/120,033

(22) Filed: Aug. 31, 2018

(65) Prior Publication Data

US 2020/0069933 A1 Mar. 5, 2020

(51) Int. Cl.
*A61M 39/20* (2006.01)
*A61M 5/14* (2006.01)
(Continued)

(52) U.S. Cl.
CPC .......... *A61M 39/20* (2013.01); *A61M 5/1411* (2013.01); *A61M 5/165* (2013.01); *A61M 5/16813* (2013.01); *A61M 5/385* (2013.01); *A61M 39/28* (2013.01); *A61M 2005/1402* (2013.01); *A61M 2205/584* (2013.01)

(58) Field of Classification Search
CPC .... A61M 39/20; A61M 39/00; A61M 39/287; A61M 2005/1402; A61M 2005/3215; A61M 2039/205; A61M 5/1411; A61M 5/1415; A61M 5/1418; A61M 5/1417; A61M 5/385; A61M 5/1414; A61M 5/3202; A61M 39/28; A61M 2005/1401; A61M 5/165; A61M 5/16813; A61M 2205/84; A61M 2025/024; A61J 1/2034; A61J 1/1462; F16B 2/02; F16B 2/04; F16B 2/06; F16B 2/10; F16L 33/02; F16L 33/021; F16L 33/03; F16L 33/025
See application file for complete search history.

(56) References Cited

U.S. PATENT DOCUMENTS

| | | |
|---|---|---|
| 5,005,793 A | 4/1991 | Shillington |
| 2002/0068905 A1 | 6/2002 | Cowan et al. |

(Continued)

OTHER PUBLICATIONS

International Search Report and Written Opinion for Application No. PCT/US2019/042062, dated Oct. 30, 2019, 14 pages.

(Continued)

*Primary Examiner* — Kevin C Sirmons
*Assistant Examiner* — Alexandra Lalonde
(74) *Attorney, Agent, or Firm* — Morgan, Lewis & Bockius LLP

(57) ABSTRACT

A device for coupling to a fluid connector of an IV administration set to resist contamination of the fluid connector and IV administration set and permit priming of the IV administration set. The device including a cover body having a cavity for receiving the fluid connector, a priming passage for priming fluid from the IV administration set through the fluid connector, and a coupling tab extending from the cover body, the coupling tab permitting the cover body to be coupled to a length of an IV line or other portion of the IV administration set to resist contamination and permit priming of the IV administration set.

21 Claims, 10 Drawing Sheets

(51) Int. Cl.
    *A61M 5/165*        (2006.01)
    *A61M 5/168*        (2006.01)
    *A61M 5/38*          (2006.01)
    *A61M 39/28*        (2006.01)

(56) References Cited

U.S. PATENT DOCUMENTS

| | | | | |
|---|---|---|---|---|
| 2007/0093762 A1* | 4/2007 | Utterberg | ............ | A61M 1/367 |
| | | | | 604/256 |
| 2008/0287920 A1 | 11/2008 | Fangrow et al. | | |
| 2009/0281502 A1* | 11/2009 | Heitkamp | ............ | A61M 25/02 |
| | | | | 604/179 |
| 2010/0200706 A1* | 8/2010 | Harding | ............ | A61J 1/00 |
| | | | | 248/62 |
| 2010/0294271 A1 | 11/2010 | Pittaway et al. | | |
| 2011/0178464 A1 | 7/2011 | Rawls | | |
| 2011/0190733 A1 | 8/2011 | D'Lima et al. | | |
| 2013/0331776 A1 | 12/2013 | Klein et al. | | |
| 2015/0073304 A1 | 3/2015 | Millerd | | |
| 2015/0306369 A1* | 10/2015 | Burkholz | ............ | A61M 39/16 |
| | | | | 604/539 |
| 2016/0279347 A1* | 9/2016 | Staley | ............ | A61M 5/385 |
| 2016/0279860 A1 | 9/2016 | Staley et al. | | |
| 2016/0339226 A1* | 11/2016 | Sealfon | ............ | A61M 39/12 |
| 2017/0080203 A1 | 3/2017 | Yeh et al. | | |
| 2018/0021511 A1* | 1/2018 | Fukuoka | ............ | A61M 5/162 |
| | | | | 604/256 |
| 2019/0247642 A1* | 8/2019 | Karthikeyan | ....... | A61M 39/105 |

OTHER PUBLICATIONS

Chinese Office Action for Application No. 201910813400.7, dated Jun. 24, 2022, 20 pages including translation.
Indian Office Action for Application No. 202137004911, dated Oct. 6, 2022, 8 pages.

* cited by examiner

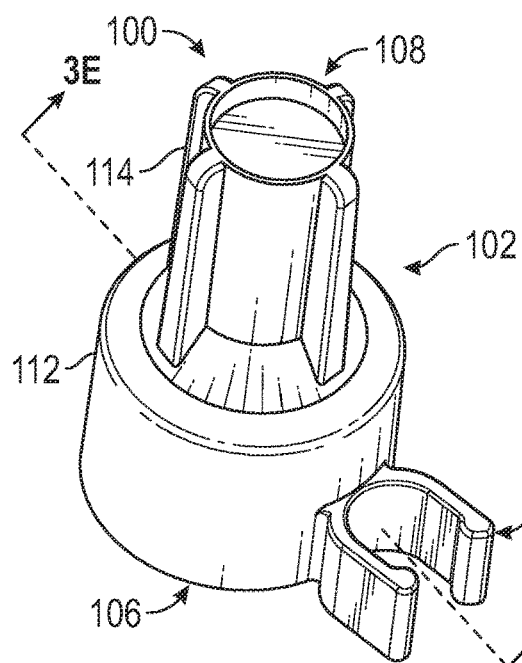
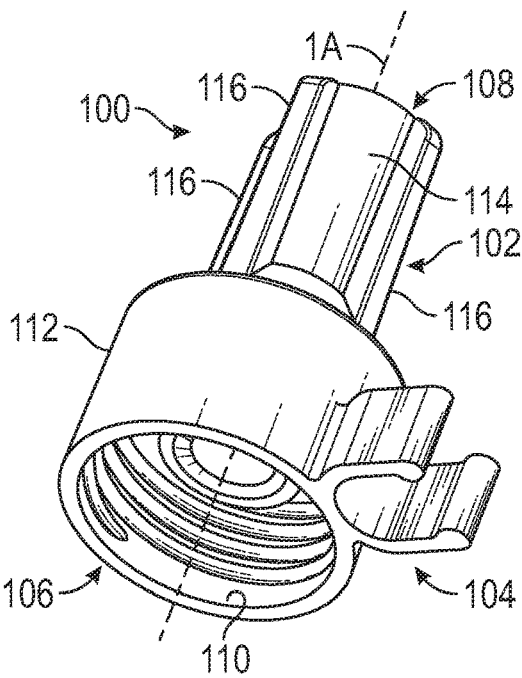
FIG. 3A
FIG. 3B
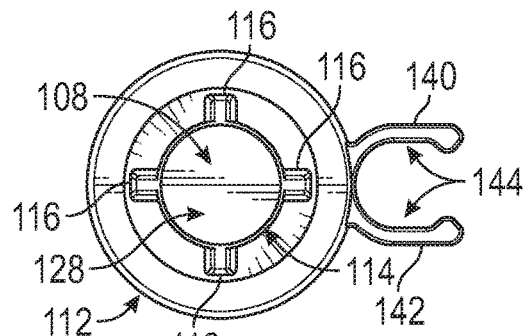
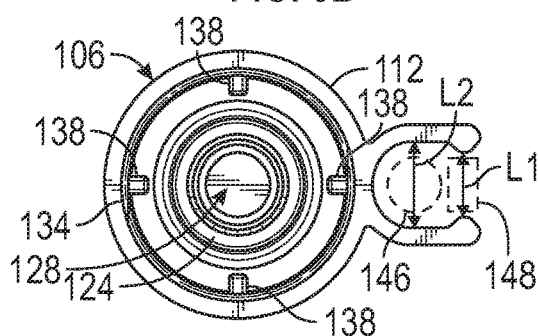
FIG. 3C
FIG. 3D
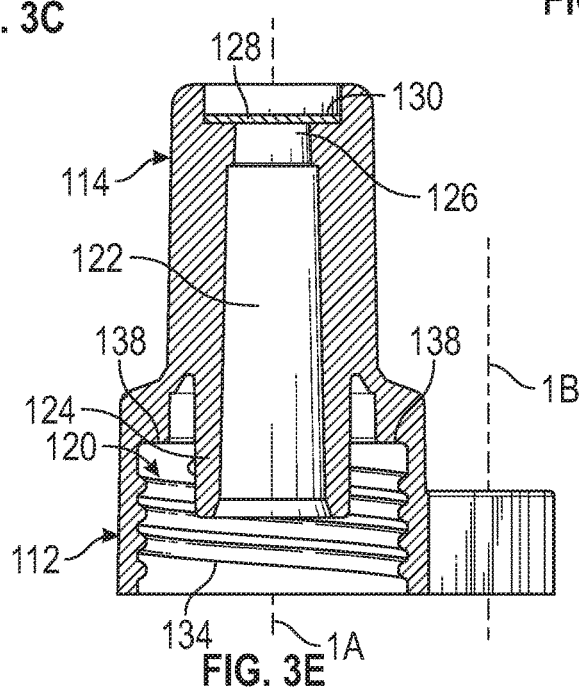
FIG. 3E

INTRAVENOUS PRIMING CAP

BACKGROUND

The present application relates to intravenous (IV) administration sets and devices used to administer fluids to a patient's vascular system through a needle or catheter inserted into a vein. More specifically, the present application is directed to fluid connector caps that can be used to cover a fluid connector, permit fluid priming, and prevent contamination of a fluid connector and IV administration set.

IV administration sets are devices used to administer fluids from a container to a patient's vascular system through a needle or catheter inserted into a vein. IV administration sets can include a needle or Luer connector, IV line or tubing, a flow regulator, a drip chamber, an infusion line filter, an intravenous set stopcock or valve, connectors between parts of the set, access ports or injection sites, a clamp such as a roller clamp, and an IV spike to penetrate and connect the tubing to an IV bag or other infusion fluid container.

SUMMARY

To prevent an air embolism, IV administration sets must be primed with a fluid or IV solution to remove air from the tubing prior to attaching the IV tubing to a patient. An air embolism is a potential complication of IV therapy and can enter a patient's blood system through unprimed IV tubing, damaged or cut tubing, access ports, and drip chambers with too little fluid.

To prime an IV administration set, a clamp is positioned along the IV line below the drip chamber, and the clamp is moved to a closed position. If present, the protective cover on the IV spike is removed, and the IV spike is inserted into an infusion fluid container. The infusion fluid container is hung or suspended, usually from an IV pole. The drip chamber can be squeezed or compressed to eject infusion fluid into and partially fill the drip chamber with the infusion fluid.

The clamp is moved to an open position to permit the infusion fluid and gas or air to move through the IV line to the distal end of the IV line, e.g., and infusion fluid container. If a cap is affixed to the distal end of the IV line, or fluid connector at the distal end of the IV line, the cap is removed to permit fluid and gas to exit the IV administration set.

To dispose of infusion fluid ejected from the IV line during priming, the distal end of the IV line can be held by a caregiver over a sink or basin. The infusion fluid is permitted to drip from the distal end of the tubing until there are no large air bubbles in the intravascular administration set. During priming of the IV administration set, a caregiver can also hold the distal end of the tubing in an inverted position while the infusion fluid moves toward the distal end of the tubing and until no air bubbles remain in the tubing. After the IV administration set is primed, the distal end of the tubing, or fluid connector affixed thereto, must be covered to prevent contamination of the IV administration set.

Priming of an IV administration set can require the caregiver to hold the distal end of the tubing in an inverted position for 10-30 seconds. This process of priming IV administration sets may be repeated many times per work shift and for multiple patients, preventing the caregiver from attending to other tasks, increasing the potential for errors such as contamination of the IV administration set, and exacerbating the required physical exertion, which can cause injury to the caregiver.

During preparation and priming, an IV administration set could become contaminated if a cap is removed from the distal end of the IV line or fluid connector, and the distal end of the IV line or fluid connector touch the ground or another object. An IV administration set could also become contaminated if a cap, removed from the distal end of the IV line or fluid connector, becomes contaminated while removed and is then reattached to the distal end of the IV line or fluid connector of the IV administration set.

Priming of an IV administration set can cause the caregiver to be exposed to the intravenous fluid being ejected from the tubing. Exposure or contact with the intravenous fluid may be harmful to the caregiver, such as when the intravenous fluid is a toxic chemotherapy drugs for use in oncology. Harm from exposure may occur in a single instance of exposure, or from repeated exposure to intravenous fluid.

In accordance with at least some embodiments disclosed herein is the realization that although a procedures can be implemented to prevent contamination of an IV administration set, certain problems occur when an innumerable number of IV administration sets are implemented during medical procedures. For example, the IV administration set can become contaminated, and the contamination can be transferred to a patient when the IV administration set is primed and coupled to a patient's intravascular system.

Some embodiments disclosed herein relate to the realization that countless IV administration sets are implemented by caregivers, who can become physically fatigued by repeated preparation and priming of IV administration sets. Embodiments disclosed herein also relate to the realization that a caregiver can become injured from exposure to the infusion fluid.

In accordance with at least some embodiments disclosed herein, the present disclosure provides IV priming caps that can prevent contamination of an IV administration set, ease physical exertion by a caregiver, reduce the time used by a caregiver for preparation and priming of an IV administration, and prevent harm to a caregiver by exposure to infusion fluids.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures:

FIG. 3A is a top perspective view of an IV priming cap, according to some embodiments.

FIG. 3B is a bottom perspective view of the IV priming cap of FIG. 3A.

FIG. 3C is a top view of the IV priming cap of FIG. 3A.

FIG. 3D is a bottom view of the IV priming cap of FIG. 3A.

FIG. 3E is a cross-sectional view of the IV priming cap of FIG. 3A.

DETAILED DESCRIPTION

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings, and detailed description are to be regarded as illustrative in nature and not as restrictive.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

In accordance with at least some embodiments disclosed herein is a IV priming cap that can prevent contamination of an IV administration set, including preventing contamination that can occur during preparation of an IV administration set and a patient, priming of the IV administration set, and coupling of the IV administration set to the patient.

Figure 2:
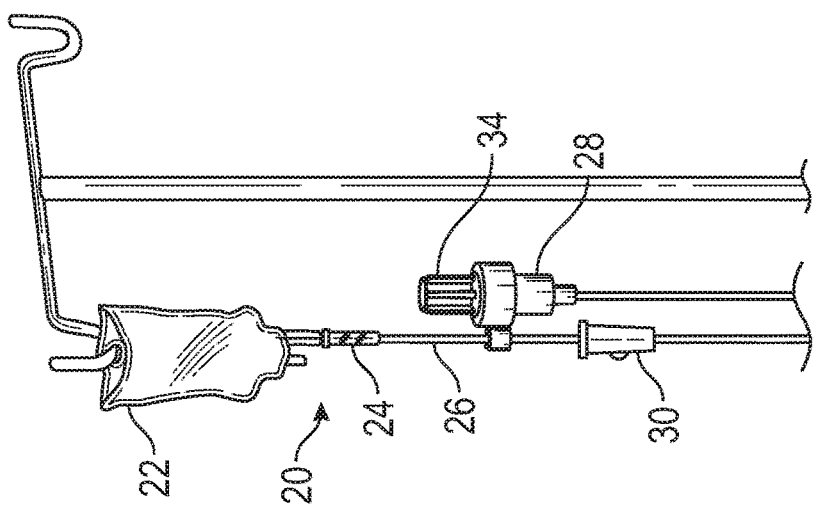
FIG. 2 is a perspective view of an infusion fluid container and an IV administration set.
Figure 1:
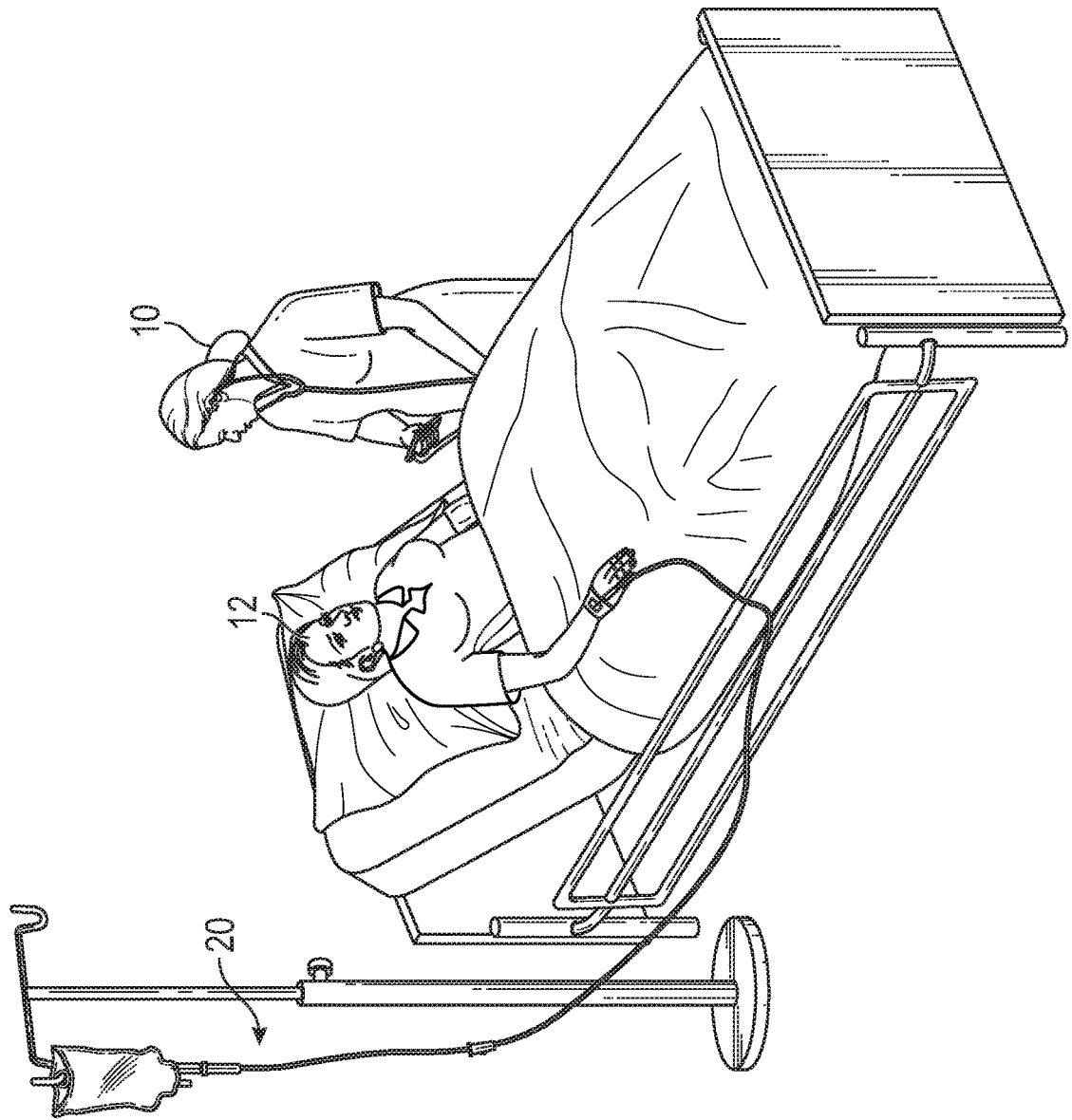
FIG. 1 is a perspective view of a patient receiving infusion fluid through and an IV administration set.

FIG. 1 illustrates a caregiver 10 and a patient 12. The patient is receiving infusion fluid through and an IV administration set 20 coupled to the patient's vascular system. FIG. 2 illustrates an infusion fluid container 22 and an IV administration set 20. The IV administration set includes a drip chamber 24 coupled to the infusion fluid container 22, tubing of an IV line 26 with a proximal end coupled to the drip chamber 24, and a distal end of the IV line 26 coupled to a fluid connector 28. A roller clamp 30 is coupled to a length of the IV line 26, between the drip chamber 24 and the fluid connector 28. The fluid connector is coupled to an IV priming cap 34, and the IV priming cap 34 is coupled to a length of the IV line 26, between the drip chamber 24 and the roller clamp 30. In some embodiments, the IV priming cap 34 can engage or couple with another portion of an IV administration set 20, such as the roller clamp 30 or an IV line pinch clamp, to hang the distal end of the IV line and fluid connector from the IV administration set.

The IV priming cap is configured so that the distal end of the IV line and fluid connector are inverted relative to the orientation of the proximal end of the IV line when the IV priming cap is coupled to the IV administration set. The inverted orientation of the distal end of the IV line and fluid connector facilitate priming of the IV administration set.

The IV priming cap can coupled to the IV administration set using a coupling tab extending from the IV priming cap. The coupling tab can be configured with one or more arm forming any of a tubing passage and a slot.

The tubing passage and/or slot can include a width that permits coupling of the IV priming cap to a length of IV tubing without compressing the IV line such that a rate of fluid flow is not reduced therethrough. However, in some embodiments, the tubing passage and/or slot can include a width that causes the length of IV line to be compressed, thereby causing a rate of fluid flow to be reduced therethrough.

In some aspects of the present disclosure, a length of IV line is compressed by an IV priming cap such that a rate of fluid flow through the IV line can permit priming of the IV administration set, however, said rate of fluid flow through the IV line is not sufficient to administer the infusion fluid to the patient. As a result, the caregiver can prime the IV administration set with the IV priming cap attached to the IV line, however, the caregiver may not achieve the desired flow rate for therapy. Because the desired flow rate is not achieved, the caregiver is prompted to remove and/or discard the IV priming cap prior to administering the infusion fluid to the patient.

The IV administration set can be primed with the distal end of the IV line with fluid connector coupled to the IV priming cap, or the IV administration set can be primed by separating the fluid connector from the IV priming cap. The IV priming cap can be separated from the IV administration set and disposed of before or after priming the IV administration set.

In some embodiments of the present disclosure, the IV priming cap can provide an indication of priming, including an indication that priming has occurred. For example, the IV priming cap can include a material that changes color to indicate that fluid has been ejected from the IV administration set. In some embodiments, the IV priming cap includes a hydrophobic filter that can change color to indicate contact with a liquid. The IV priming cap can also provide an indication that the IV priming cap remains coupled to the IV administration set. For example, the IV priming cap can be configured to restrict fluid flow through the IV line as an indication to remove the IV priming cap.

Although the present disclosure describes embodiments of an IV priming cap that can couple with a male luer-type fluid connector, it should be appreciated that the IV priming cap can be coupled with other fluid connectors. However, for clarity and brevity, the present disclosure will primarily refer to a male luer fluid connector. Additionally, although the present disclosure describes of an IV priming cap relative to an IV administration set, it should be appreciated that the IV priming cap can be coupled with other IV fluid delivery devices and systems. However, for clarity and brevity, the present disclosure will primarily refer to an IV administration set.

FIGS. 3A-3E illustrate an embodiment of an IV priming cap 100. The IV priming cap can couple with a distal end of an IV line, or fluid connector at the distal end of the IV line. In at least some embodiments disclosed herein, the IV priming cap could couple with a fluid connector and a portion of an IV administration set to suspend the distal end of the IV line and fluid connector from the IV administration set.

The IV priming cap 100 includes a cover body 102 and a coupling tab 104. The cover body 102 includes a proximal end 106 and a distal end 108, opposite the proximal end 106. The cover body 102 includes an inner surface 110 defining a cavity extending into the cover body 102 and configured to receive a fluid connector therein. The cavity can extend from the proximal end 106 toward the distal end 108 of the cover body 102. A longitudinal connector cavity axis 1A extends between the proximal end 106 and the distal end 108 of the cover body 102.

The cover body 102 has an outer surface with a cross-sectional profile, transverse to the longitudinal connector cavity axis 1A. As used in the present disclosure, the term transverse can include any direction or angle that can intersect or extend across another direction or angle. The cross-sectional profile of the cover body 102 can taper from the proximal end 106 toward the distal end 108. In some embodiments of the present disclosure, the outer surface of the cover body 102 has a proximal segment 112, extending from the proximal end 106 toward the distal end 108, and a distal segment 114, extending from the proximal segment 112 toward the distal end 108. The proximal segment 112 has a first cross-sectional width, and the distal segment 114 has a second cross-sectional width that is less than the first cross-sectional width. In some embodiments, the outer surface of the cover body 102 tapers between the proximal segment 112 and the distal segment 114.

The IV priming cap 100 can include ribs 116 protruding from the outer surface of the cover body 102, as shown in FIGS. 3A-3C. The ribs 116 can extend between the proximal end 106 and the distal end 108 of the cover body 102. In at least some embodiments disclosed herein, the ribs 116 extend along the distal segment 114, between the proximal segment 112 and the distal end 108 of the cover body.

The ribs 116 can provide increased surface area and leverage for grasping and rotating the IV priming cap 100 around the longitudinal connector cavity axis 1A. The ribs 116 can also provide structural rigidity and support along the proximal segment 112 and the distal segment 114.

In some embodiments, the outer surface of the cover body 102 can include grooves or channels that extend into the outer surface of the cover body 102. In at least some embodiments of the present disclosure, the outer surface of the cover body 102 can include a concave portion, such as a dimple or notch, a convex portion, such as a bulge or ridge, or any combination thereof. Any of the concave and the convex surface features can increase the surface area of the outer surface area and increase rigidity of the cover body 102.

The inner surface 110 of the cover body can form a proximal cavity 120 along the proximal segment 112 of the cover body, and a distal cavity 122 along the distal segment 114 of the cover body, as best illustrated in FIG. 3E.

When the IV priming cap 100 is coupled with a fluid connector, different portions of the fluid connector may engage the cover body 102 at the proximal cavity 120 and the distal cavity 122. In some examples, when a male luer connector is coupled with the IV priming cap 100, a body portion of fluid connector may be positioned within the proximal cavity 120, and the male luer portion of the fluid connector may be positioned within the distal cavity 122. In an example, an outer surface of the fluid connector having a thread or other coupling feature can engage the inner surface 110 of the cover body along the proximal cavity 120. When the coupling feature of the fluid connector is engaged against the inner surface 110 of the cover body along the proximal cavity 120, the male luer portion of the fluid connector may engage against the inner surface 110 of the cover body along the distal cavity 122.

The cover body 102 can include a wall 124 that extends from the distal segment 114 into the proximal cavity 120, and around the connector cavity axis 1A. An inner surface of the wall 124 can form a portion of the distal cavity 122. An outer surface of the wall 124 is spaced apart from the inner surface 110 of the cover body along the proximal segment 112.

The distal cavity 122 has a cross-sectional width, formed between the inner surface of the distal cavity 122 and the wall 124. The cross-sectional width of the distal cavity 122 can be configured to engage against a male luer of a fluid connector inserted into the cavity of the cover body 102. The cross-sectional width of the distal cavity 122 can taper toward the distal end 108 of the cover body. In some aspects of the present disclosure, the IV priming cap 100 can fluidly seal against a male luer of a fluid connector by forming an interference fit between the male luer and the inner surface of the cover body 102 along the distal cavity 122.

The cover body 102 can include a priming passage 126 to permit movement of a fluid between the cavity of the cover body 102 and an area adjacent to the outer surface of the IV priming cap 100. The priming passage 126 extends between the distal cavity 122 and the distal end 108 of the cover body. In some embodiments, the priming passage 126 can extend from any of the proximal cavity 120 and/or distal cavity 120 to an outer surface of the cover body 102. In some examples, the priming passage 126 extends between the distal cavity 120 and an outer surface side surface of the cover body along the distal segment 114. In some embodiments, at least a portion of the priming passage 126 can be formed by a groove extending into the cover body 102.

The priming passage 126 permits priming of the IV administration set without separating or removing the IV priming cap 100 from the fluid connector. As a result, infusion fluid and gasses can be directed out of the IV administration set through the fluid connector with the IV priming cap 100 affixed thereto. Because the IV priming cap 100 does not need to be removed or separated from the fluid connector during priming, the potential of contaminating the fluid connector or IV administration set is reduced.

In at least some embodiments disclosed herein, the IV priming cap 100 comprises a filter 128. The filter 128 is positioned along the priming passage 126 to strain or separate a fluid moving therethrough. In some embodiments of the present disclosure, the filter 128 can provide an indication that the IV administration set has been used and/or primed.

Figure 4A:
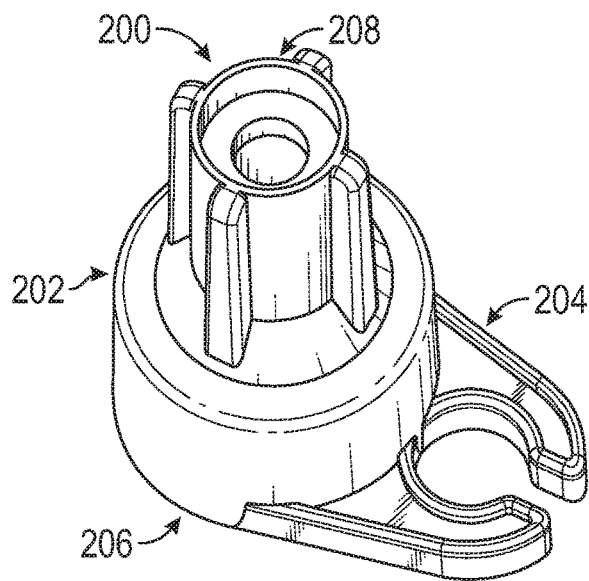
FIG. 4A is a top perspective view of another embodiment of an IV priming cap, according to some embodiments.
Figure 4B:
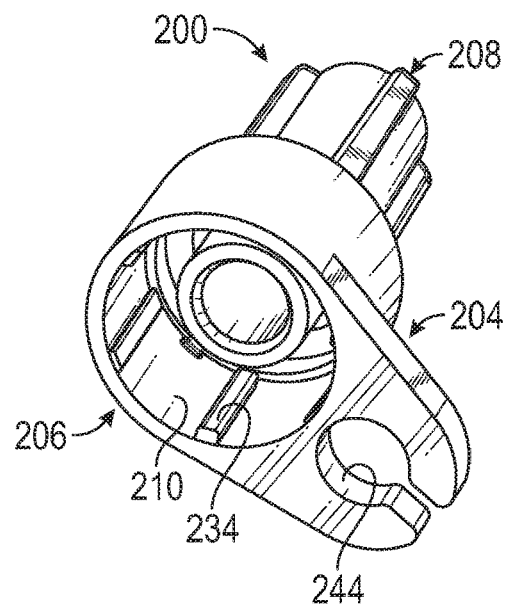
FIG. 4B is a bottom perspective view of the IV priming cap of FIG. 4A.
Figure 4C:
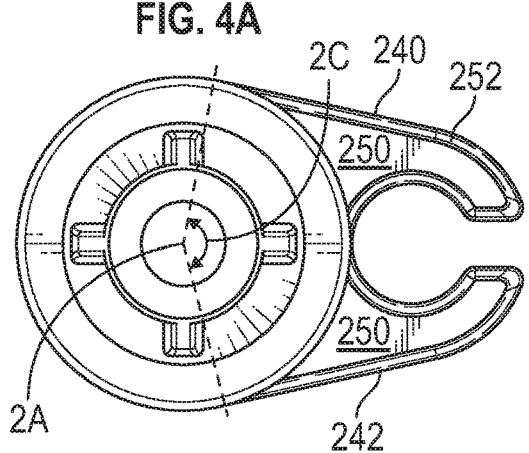
FIG. 4C is a top view of the IV priming cap of FIG. 4A.

The filter 128 can be positioned within the priming passage 126, or coupled to a tip portion of the cover body 102. Referring to FIG. 3E, the IV priming cap can include a recess 130 to receive the filter 128 therein. The recess 130 can extend into the distal end of the cover body 102 and the priming passage 126 intersects the recess 130. In some embodiments, the IV priming cap does not include a filter. In embodiments which do not include a filter, the priming passage can extend through the recess 130 (e.g., FIG. 4E).

The filter 128 can be configured to permit a gas to move through the filter while resisting movement of a liquid through the filter. For example, the filter 128 can be a hydrophobic filter. In some examples, the filter 128 comprises polyethylene material, or comprises a membrane coated with polyethylene.

To provide an indication that the IV administration set has been used and/or primed, the filter can comprise a color that changes. For example, the filter may change color when a liquid (e.g., infusion fluid) has contact against the filter.

At least some embodiments disclosed herein, the inner surface of the cover body 102 includes a ridge 134 configured to engage against a fluid connector positioned within the cavity of the IV priming cap. The ridge 134 can be formed as any of a helical ridge and a longitudinal ridge. In some embodiments, the ridge 134 can be any shape configured to engage with a fluid connector.

The helical ridge (e.g., FIGS. 3B and 3E) can be shaped as a thread along the inner surface of the cover body. The thread can extend away from the inner surface or into the inner surface 110 of the cover body. The thread can have a thread pitch configured to mesh with a thread of a fluid connector coupled to IV priming cap.

The longitudinal ridge (e.g., FIGS. 4B and 4E) can be shaped as any of a wall extending longitudinally along the inner surface of the cover body, and a groove or channel extending into the inner surface 110 of the cover body. In some aspects, a ridge can be formed between channels extending into the inner surface 110 of the cover body. The longitudinal ridge can be configured to engage against an outer surface of a fluid connector coupled to IV priming cap.

In some embodiments of the present disclosure, any of the helical and longitudinal ridge can be shaped as a plurality of plurality of protrusions in a helical or angular pattern relative to the connector cavity axis A1, and can extend parallel with the connector cavity axis A1.

The cover body 102 can include a projection 138 extending into any of the proximal cavity 120 and the distal cavity 124. The projection 138 can extend from the inner surface 110 of the cover body into the proximal cavity 120. FIGS. 3D and 3E, the projection 138 extends form the inner surface 110, between the proximal segment 112 and the distal segment 114 of the cover body. In some embodiments, projections 138 are spaced apart around the connector cavity axis A1.

The projection 138 can resist movement of a fluid connector, within the proximal cavity 120, in a direction toward the distal cavity 122. In some aspects, the projection 138 can provide rigidity between the proximal segment 112 and the distal segment 114 of the cover body.

The coupling tab 104 of the IV priming cap 100 is generally shaped as a clamp extending from the cover body 102 to engage or couple with a portion of the IV administration set. When the coupling tab 104 is coupled with the IV administration set, the distal end of the IV line and fluid connector retained within the IV priming cap are covered to resist contamination from contact by a caregiver or patient. Further, the distal end of the IV line and fluid connector are suspended from the IV administration set, preventing contamination from contact with the floor or ground. Further yet, the inverted orientation of the distal end of the IV line and fluid connector, when the IV priming cap is coupled to the IV administration set, facilitated priming of the IV administration set.

The coupling tab 104 is shaped as a clamp having a first coupling arm 140 and a second coupling arm 142. Each of the first coupling arm 140 and the second coupling arm 142 include a base portion coupled to the cover body 102 and a tip portion distal to the cover body 102. The coupling tab 104 extends away from the cover body 102 in a direction that is transverse relative to the connector cavity axis 1A.

Each of the first coupling arm 140 and the second coupling arm 142 include an inner surface 144 facing toward the other of the first coupling arm 140 and the second coupling arm 142. The inner surface of the first coupling arm 140 and the second coupling arm 142 form a tubing passage 146 therebetween, identified generally by the area in broken lines in FIG. 3D.

The inner surface of the first coupling arm 140 and the second coupling arm 142 also form at least a portion of a slot 148, identified generally by the area in broken lines in FIG. 3D. The slot 148 extends between the tubing passage 146 and the outer surface of the coupling tab 104 to permit a length of IV line to be moved into the tubing passage 146. The slot 148 can also permit the coupling tab 104 to couple with another structure. In some embodiments, the slot extends from a tip portion toward the base portion of the coupling tab 104.

A portion of the inner surface of the first coupling arm 140 and the second coupling arm 142 along the slot 148 extends inward such that a length L1 between the inner surfaces 144 along the slot 148 is less than a length L2 between the inner surfaces 144 along the tubing passage 146. The length L1 can be approximately equal to or less than a diameter of the IV line. In use, the first coupling arm 140 and the second coupling arm 142 can be urged away from each other to permit a length of IV tubing to be moved through the slot and into the tubing passage 146.

A longitudinal tubing passage axis 1B extends through the tubing passage 146 and is parallel to the longitudinal connector cavity axis 1A. When the coupling tab 104 is coupled with a length of IV line, the length of IV line will extend generally aligned along the longitudinal tubing passage axis 1B, and the distal end portion of the IV line will be generally aligned along the longitudinal connector cavity axis 1A. In some embodiments, the longitudinal tubing passage axis 1B extends at an angle that is transverse relative to the connector cavity axis 1A, wherein transverse includes any angle that extends across the connector cavity axis 1A.

In some embodiments of the present disclosure, the IV priming cap 200 includes a coupling tab 204 having opposing coupling arms, as illustrated in FIGS. 4A-4E.

The IV priming cap 200 can include features similar to those described with reference to the IV priming cap 100 (FIGS. 3A-3E). As such, a description of some similar features is not repeated herein for clarity and brevity. However, features described with reference to an embodiment of the present disclosure can be implemented with any embodiment of the present disclosure.

The IV priming cap 200 includes a cover body 202 and a coupling tab 204. The cover body 202 includes a proximal end 206 and a distal end 208, opposite the proximal end 206. The cover body 202 includes an inner surface 210 defining a cavity extending into the cover body 202 and configured to receive a fluid connector therein. A longitudinal connector cavity axis 2A extends between the proximal end 206 and the distal end 208 of the cover body 202.

The inner surface 210 includes ridges 234 configured to engage against a fluid connector positioned within the cavity of the IV priming cap. The ridges 234 are shaped as longitudinal ridges that can create an interference fit between the IV priming cap 200 and a fluid connector inserted into the cavity. In some aspects, the ridges 234 are configured to mate with or engage a slot of the fluid connector.

The ridges 234 extend between the proximal end 206 and the distal end 208 of the cover body 202, and are aligned relative to a connector cavity axis 2A. Each of the ridges 234 extend parallel to the connector cavity axis 2A, however, in some embodiments, ridges 234 can extend transverse to the connector cavity axis 2A. For example, ridges 234 can extend transverse to the connector cavity axis 2A to form a spiral of ridges along the inner surface.

The ridges 234 can be spaced apart from each other along the inner surface of the cover body 202. The ridges 234 are spaced apart with an equal distance between each longitudinal ridge 234. In some embodiments, however, the longitudinal ridges 234 can be spaced apart with a different distance between one or more ridge. Ridges 234 having different spacing therebetween can permit a fluid connector having mating channels with similar spacing therebetween to be inserted into the IV priming cap.

The ridges 234 comprise a height between the inner surface of the cover body and an inner-most surface of each ridge 234, e.g., a surface closest to the connector cavity axis 2A. One or more of the ridges 234 can have different height relative to another longitudinal ridge 234.

Figure 4D:
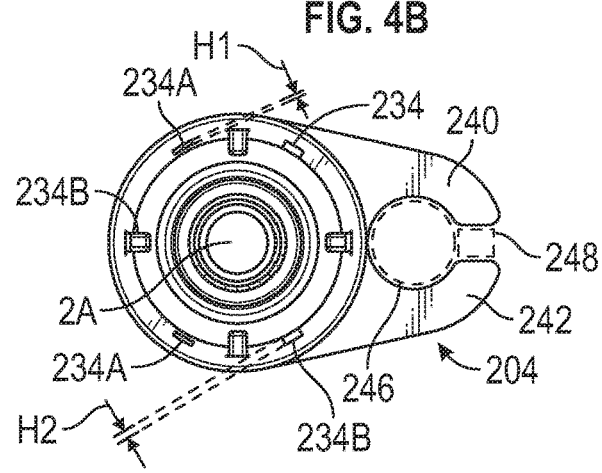
FIG. 4D is a bottom view of the IV priming cap of FIG. 4A.
Figure 4E:
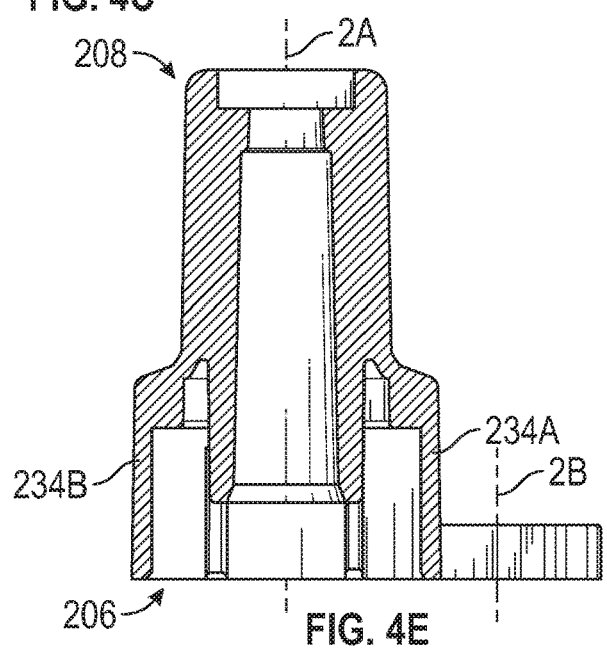
FIG. 4E is a cross-sectional view of the IV priming cap of FIG. 4A.
Figure 5A:
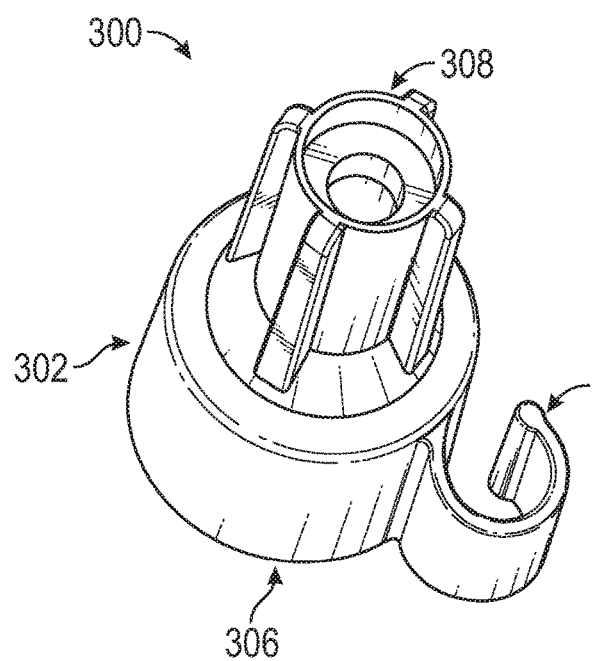
FIG. 5A is a top perspective view of another embodiment of an IV priming cap, according to some embodiments.
Figure 5B:
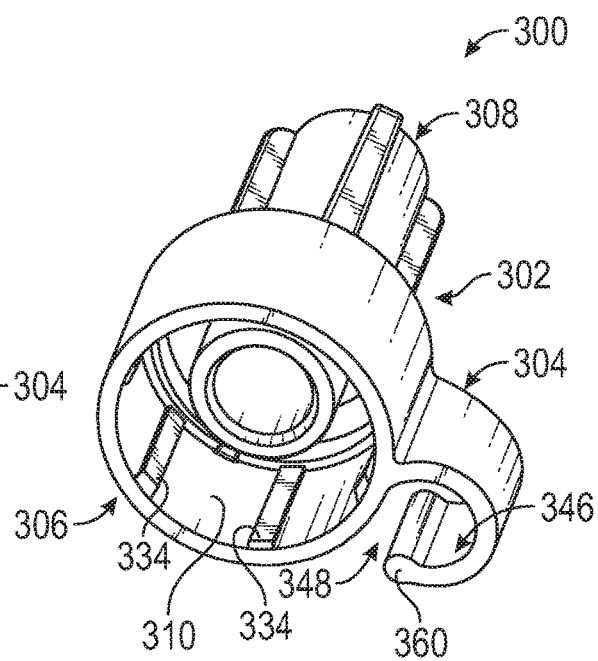
FIG. 5B is a bottom perspective view of the IV priming cap of FIG. 5A.
Figure 5C:
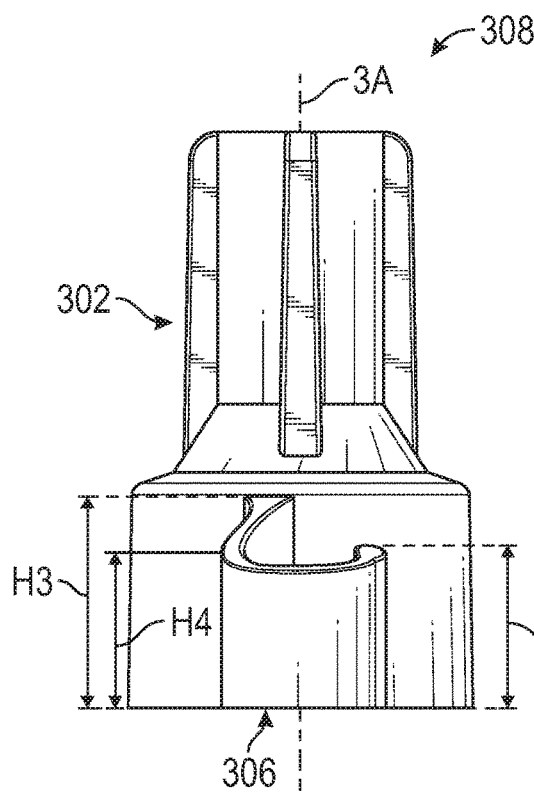
FIG. 5C is a front view of the IV priming cap of FIG. 5A.
Figure 5D:
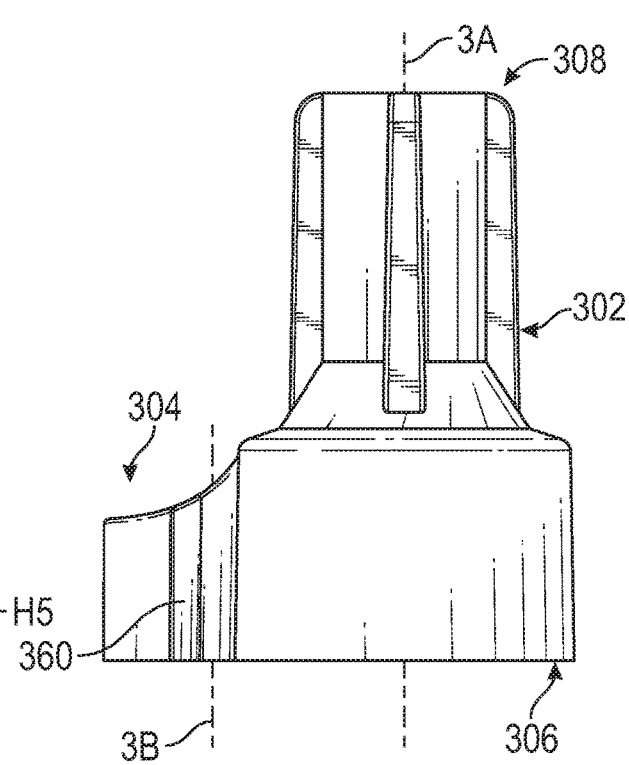
FIG. 5D is a side view of the IV priming cap of FIG. 5A.
Figure 6A:
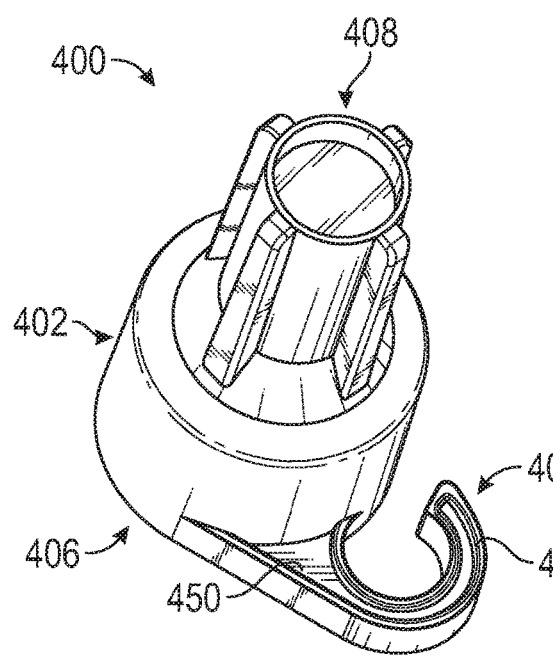
FIG. 6A is a top perspective view of another embodiment of an IV priming cap, according to some embodiments.
Figure 6B:
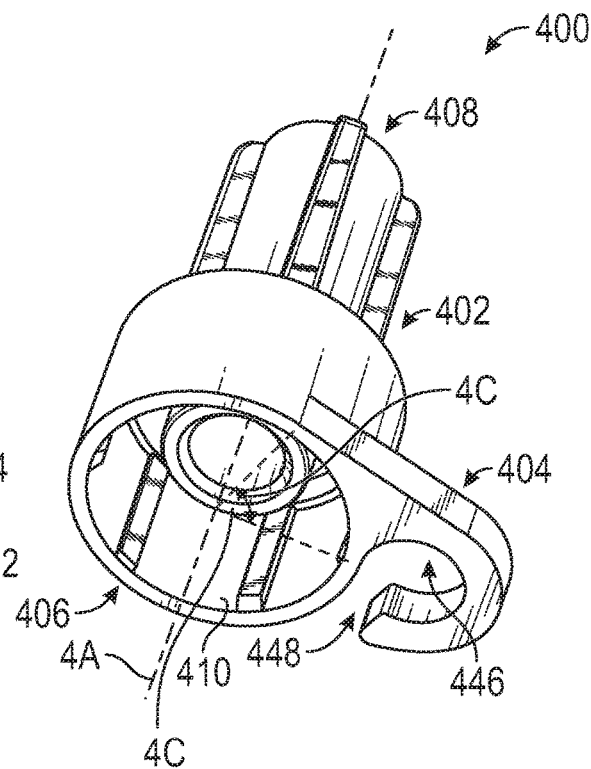
FIG. 6B is a bottom perspective view of the IV priming cap of FIG. 6A.
Figure 6C:
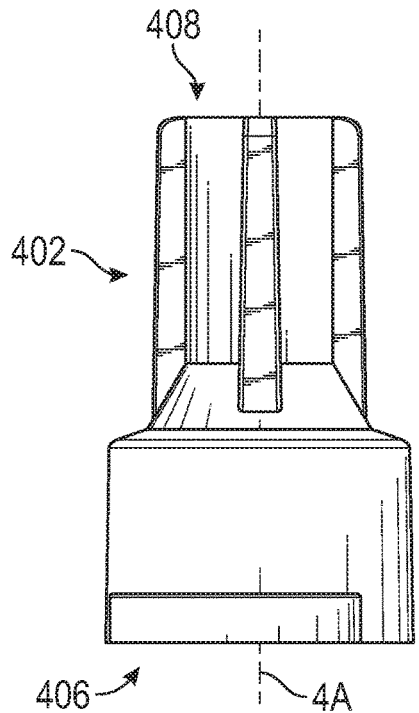
FIG. 6C is a front view of the IV priming cap of FIG. 6A.
Figure 6D:
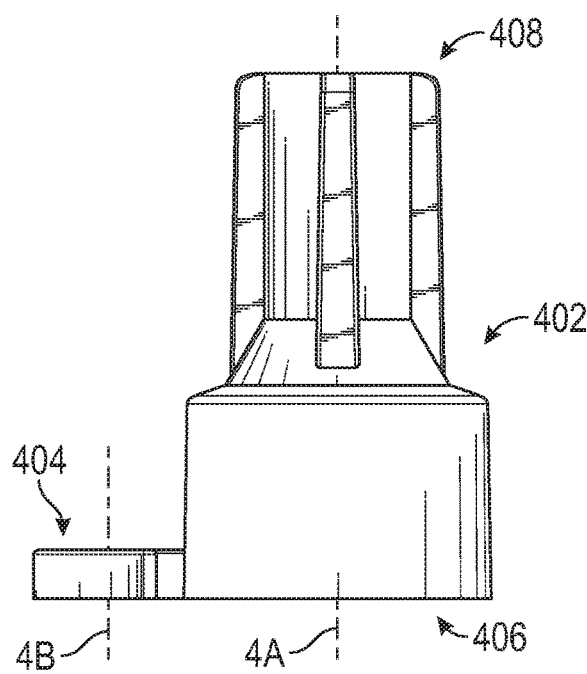
FIG. 6D is a side view of the IV priming cap of FIG. 6A.
Figure 7A:
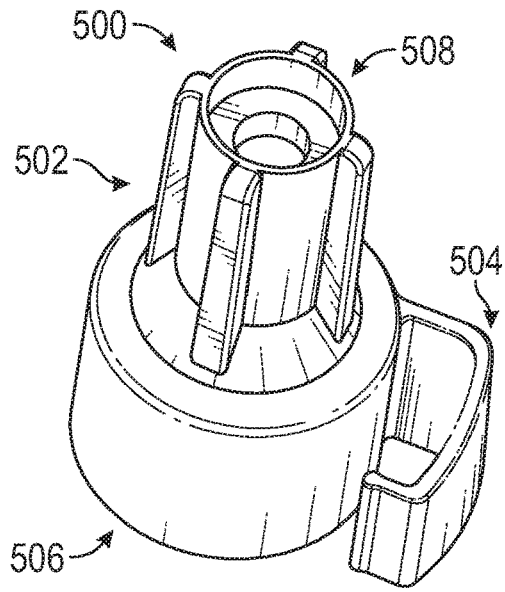
FIG. 7A is a top perspective view of another embodiment of an IV priming cap, according to some embodiments.
Figure 7B:
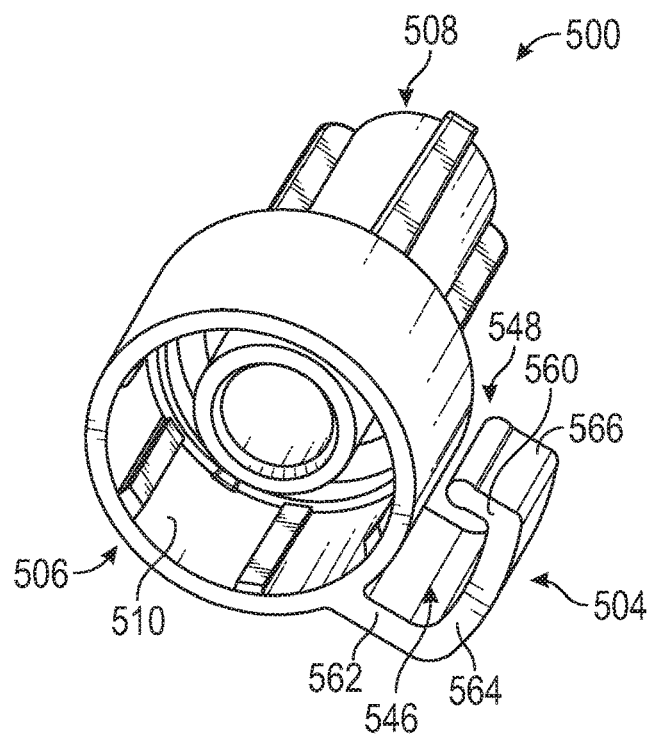
FIG. 7B is a bottom perspective view of the IV priming cap of FIG. 7A.
Figure 7C:
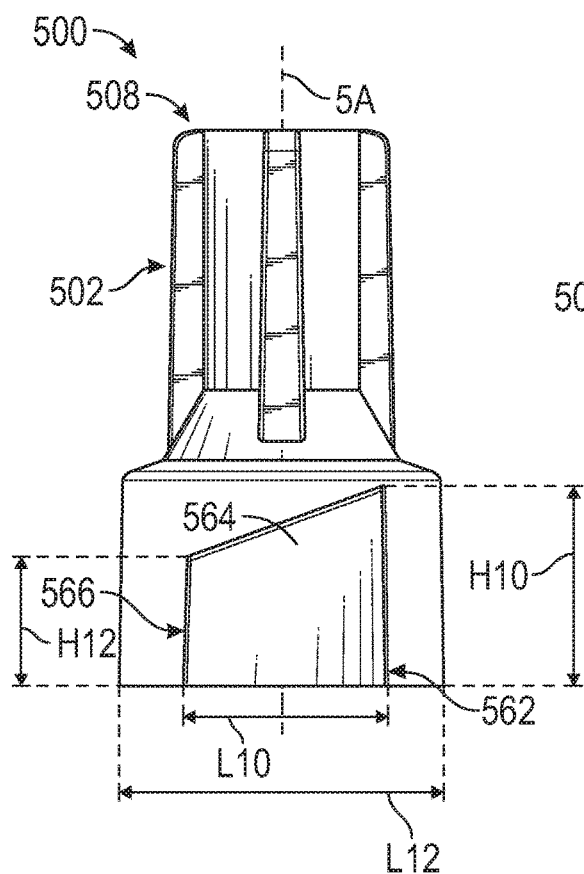
FIG. 7C is a front view of the IV priming cap of FIG. 7A.
Figure 7D:
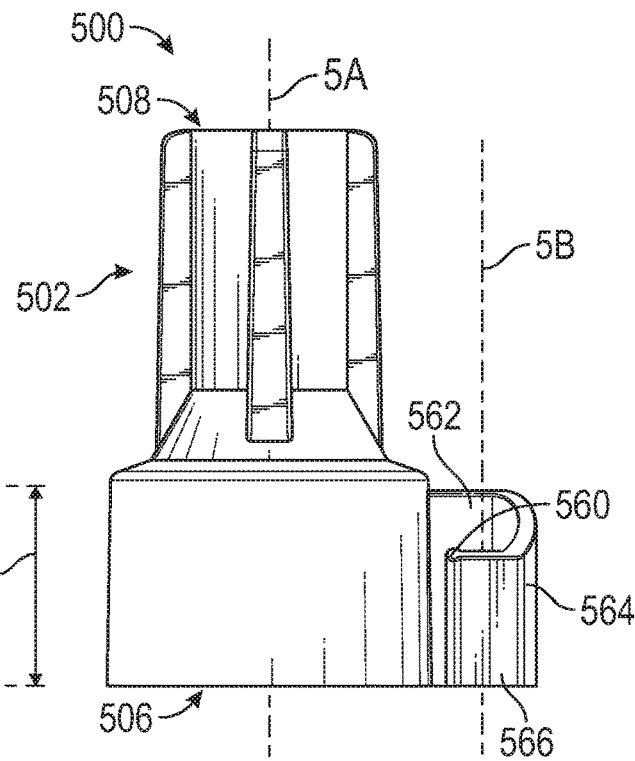
FIG. 7D is a side view of the IV priming cap of FIG. 7A.
Figure 8A:
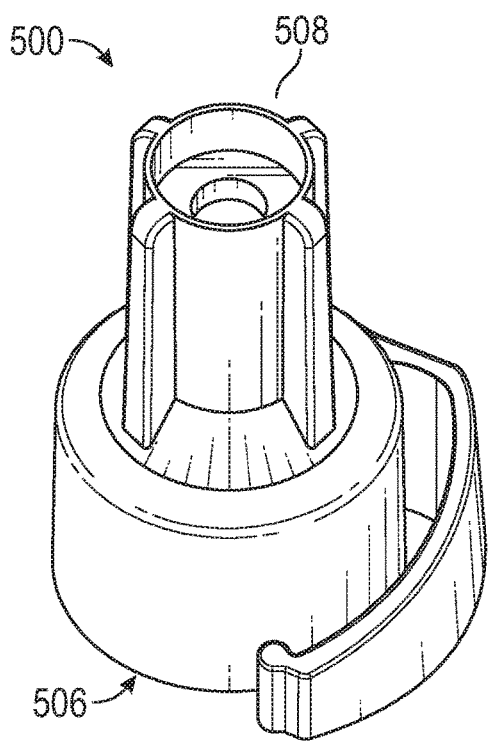
FIG. 8A is a top perspective view of another embodiment of an IV priming cap, according to some embodiments.
Figure 8B:
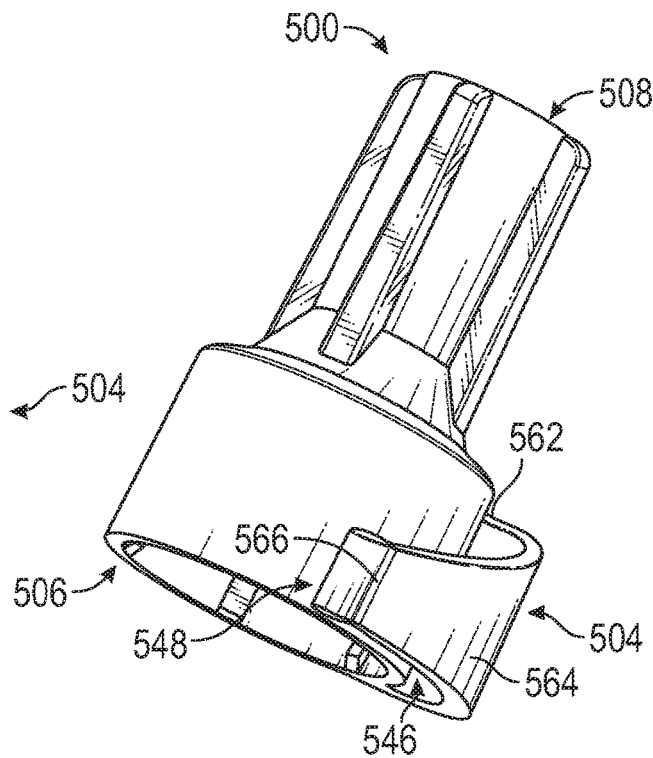
FIG. 8B is a bottom perspective view of the IV priming cap of FIG. 8A.
Figure 8C:
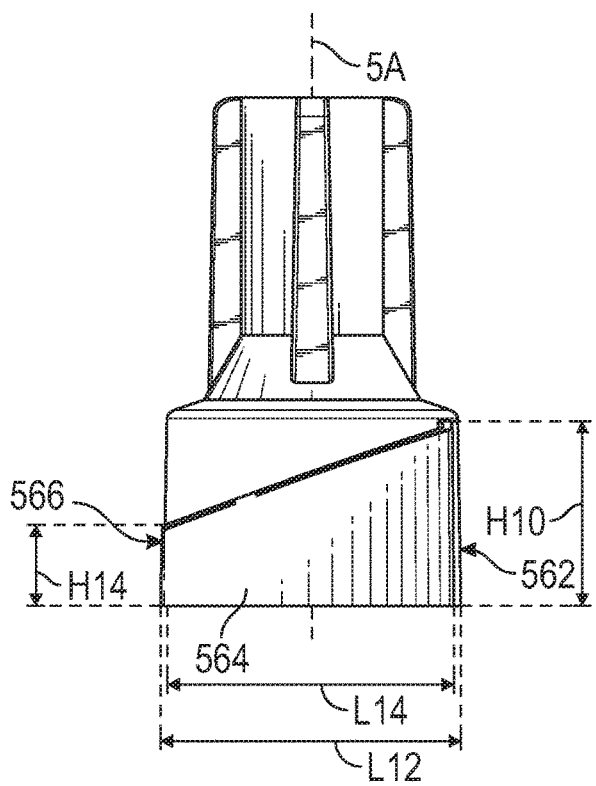
FIG. 8C is a front view of the IV priming cap of FIG. 8A.
Figure 8D:
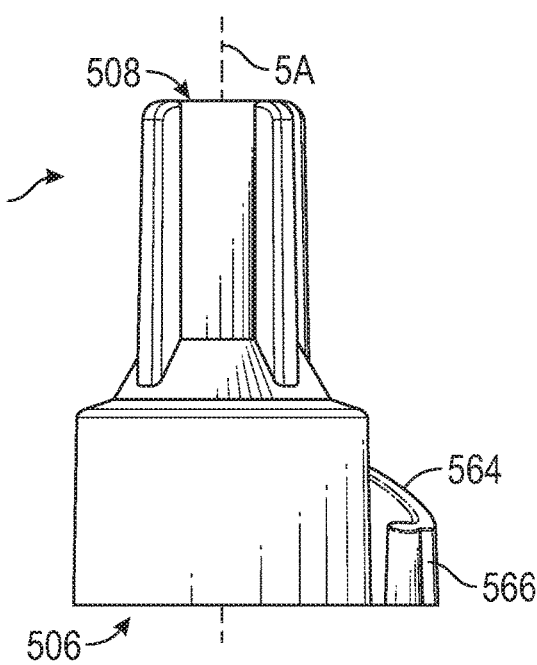
FIG. 8D is a side view of the IV priming cap of FIG. 8A.

Referring to FIG. 4D, the IV priming cap 200 can have ridges 234A having a first height H1, and a ridges 234B having a second height H2, which is greater than the first height H1. The ridges can be positioned so that ridges 234A having a first height H1 are positioned between ridges 234B having a second height H2.

In some embodiments of the present disclosure, the ridges 234 can have a height that increases or decreases between the proximal end 206 and the distal end 208. For example, the height of the ridges 234, illustrated in FIG. 4E, decreases from the proximal end 206 toward the distal end 208, such that a cross-sectional length between inner surfaces of the ridges tapers away from the proximal end 206.

The coupling tab 204 of the IV priming cap 200 extends away from the cover body 202 in a direction that is transverse relative to the connector cavity axis 2A. The coupling tab 204 has a first coupling arm 240 and a second coupling arm 242, with the second coupling arm 242 oriented opposite the first coupling arm 240 to form a lobster claw shape.

Each of the first coupling arm 240 and the second coupling arm 242 include a base portion coupled to the cover body 202 and a tip portion distal to the cover body 202. The first coupling arm 240 and the second coupling arm 242 have a width in a direction that is transverse to the connector cavity axis 2A. The width of each of the first coupling arm 240 and the second coupling arm 242 tapers from the base portion toward the tip portion.

The base portion of the first coupling arm 240 and the second coupling arm 242 extends along the outer surface of the cover body 202 over an angle 2C around the connector cavity axis 2A. In some embodiments of the present disclosure, the angle 2C is at least about 90 degrees and/or less than or equal to about 180 degrees. In some embodiments, the base portion extends along the outer surface of the cover body 202 over an angle of about 140 degrees around the connector cavity axis 2A.

The first coupling arm 240 and the second coupling arm 242 include an inner surface 244 facing toward the other of the first coupling arm 240 and the second coupling arm 242. The inner surface of the first coupling arm 240 and the second coupling arm 242 form a tubing passage 246, identified generally by the area in broken lines in FIG. 4D. A longitudinal tubing passage axis 2B extends through the tubing passage 246. The longitudinal tubing passage axis 2B extends at an angle that is parallel relative to the longitudinal connector cavity axis 2A. In some embodiments, the tubing passage axis 2B extends at an angle that is transverse relative to the longitudinal connector cavity axis 2A. The tubing passage 246 has a cross-sectional shape. The cross-sectional shape can be any of a circle, an ellipse, a semicircle, and a polygon. In some embodiments, the tubing passage 246 has a diameter that is less than a diameter of the IV line so that the coupling tab 200 engages against the IV line and resists movement between IV priming cap 200 and the IV line.

The inner surface of the first coupling arm 240 and the second coupling arm 242 also form at least a portion of a slot 248, identified generally by the area in broken lines in FIG. 4D. The slot 248 extends between the tubing passage 246 and the outer surface of the coupling tab 204. The slot 248 is positioned so that a passage formed by the slot 248, between the tubing passage 246 and the outer surface of the coupling tab 204. The slot 248 can extend from a tip portion toward the base portion of the first and second coupling arms 240 and 242.

A portion of the inner surface of the first coupling arm 240 and the second coupling arm 242 along the slot 248 extends inward such that a length between the inner surfaces 244 along the slot 248 is less than a length between the inner surfaces 244 along the tubing passage 246.

The first coupling arm 240 and the second coupling arm 242 include a proximal surface facing toward the direction of the proximal end 206, and a distal surface facing toward the direction of the distal end 208. The distal surface comprises a recessed surface 250 so that at least a portion of the perimeter of each coupling arm 240 and 242 comprises a wall 252 that extends above the recessed surface 250. In some embodiments of the present disclosure, any of the proximal surface and the distal surface of coupling arm 240 and 242 can include a recess surface. The recessed surface 250 and wall 252 provide structural rigidity while reducing the amount of material necessary to form the coupling tab 204.

The tubing passage 246 and slot 248 permit a length of IV line to be moved into the tubing passage 246. The tubing passage 246 and slot 248 can also permit the IV priming cap 200 to be coupled with another structure, such as a pole or clamp. When the coupling tab 204 is coupled with a length of IV line, the length of IV line will extend generally aligned along the longitudinal tubing passage axis 2B, and the distal end portion of the IV line will be generally aligned along the longitudinal connector cavity axis 2A.

In some embodiments of the present disclosure, the IV priming cap 300 includes a hook-shaped coupling tab 304, as illustrated in FIGS. 5A-5D.

The IV priming cap 300 can include features similar to those described with reference to other embodiments disclosed herein. As such, a description of some similar features is not repeated herein for clarity and brevity.

The IV priming cap 300 includes a cover body 302 and a coupling tab 304. The cover body 302 includes a proximal end 306 and a distal end 308, opposite the proximal end 306. The cover body 302 includes an inner surface 310 defining a cavity extending into the cover body 302 and configured to receive a fluid connector therein. A longitudinal connector cavity axis 3A extends between the proximal end 306 and the distal end 308 of the cover body 302. The cover body 302 can also include ridges 334 that extend from the inner surface 310 into the cavity to engage against a fluid connector positioned within the cavity of the IV priming cap.

The coupling tab 304 of the IV priming cap 300 extends away from the cover body 302 in a direction that is transverse relative to the connector cavity axis 3A. The coupling tab includes a base portion coupled to the cover body 302 and a tip portion distal to the cover body 302.

The base portion extends from the cover body 302 in a first direction, and the tip portion extends from the base portion in a second direction, which is different than the first direction. The first direction is transverse to the connector cavity axis 3A and extends away from the outer surface of the cover body 302. The second direction is also transverse to the connector cavity axis 3A, but extends toward the outer surface of the cover body 302. Together, the base portion and the tip portion form a hook-shaped coupling tab 304 having an inner surface forming a tubing passage 346 with a longitudinal tubing passage axis 3B therethrough. The tubing passage axis 3B is parallel relative to the longitudinal connector cavity axis 3A. In some embodiments, the tubing passage axis 3B extends at an angle that is transverse relative to the connector cavity axis 3A.

In some embodiments, the tubing passage 346 has a diameter that is less than a diameter of the IV line so that the coupling tab 304 engages against the IV line and resists movement between IV priming cap 300 and the IV line.

At least a portion of a slot 348 can be formed between the coupling tab 304 and the cover body 302. More specifically, the slot 348 can be formed between the tip portion of the coupling tab 302 and an outer surface of the cover body 304. In some embodiments, the slot 348 extends between the tubing passage 346 and the outer surface of the coupling tab 304. The slot 348 is oriented to extend, between the tubing passage 346 and the outer surface of the coupling tab 304, in a direction toward the base portion of the coupling tab 304.

A cross-section of the coupling tab 304 is shaped as a wall having a height and a width. The height of the coupling tab 304 extends between a proximal surface, facing toward the direction of the proximal end 306, and a distal surface, facing toward the direction of the distal end 308. Along the base portion of the coupling tab 304, the wall height decreases away from the cover body 302 from a first height H3 to a second height H4. Along the tip portion of the coupling tab 304, the wall height increases toward the cover body 302, from the second height H4 to a third height H5. The third height H5 is greater than the second height H4. In some embodiments, the third height H5 is between the first height H3 and the second height H4.

The width of the coupling tab 304 is less than the first height H3, the second height H4, and the third height H5. The narrow width of the coupling tab 304, relative to the height, permits the coupling tab 304 to be urged away from the tubing passage axis 3B when a length of IV line is moved through the slot 346 to the tubing passage 348. The tall height of the coupling tab 304, relative to the width, provides a large inner surface area of the coupling tab 304 to engage against the length of IV line is inserted into the tubing passage 348. Engagement of the inner surface of the coupling tab 304 resists sliding or movement of the IV line relative to the IV priming cap 300.

A tip portion of the coupling tab 304 can include a protrusion 360 having outer surfaces that extend away from the outer surfaces of the coupling tab 304. The protrusion 360 can be cylindrically shaped and extend longitudinally along the height of the coupling tab 304. In some embodiments, the protrusion 360 can comprise a cross-sectional shape that includes any of a circle, an ellipse, a semicircle, and a polygon. A cross-sectional profile of the protrusion 360, transverse to the tubing passage axis 3B, comprises a width that tapers along the height of the coupling tab 304. The width of the protrusion 360 tapers from a proximal end of the coupling tab toward a distal end of the coupling tab 304.

The tubing passage 346 and slot 348 permit a length of IV line to be moved into the tubing passage 346. The tubing passage 346 and slot 348 can also permit the IV priming cap 300 to be coupled with another structure, such as a pole or clamp. When the coupling tab 304 is coupled with a length of IV line, the length of IV line will extend generally aligned along the longitudinal tubing passage axis 3B, and the distal end portion of the IV line will be generally aligned along the longitudinal connector cavity axis 3A.

Referring to FIGS. 6A-6D, an embodiment of an IV priming cap 400 having a hook-shaped coupling tab 404 is illustrated. The IV priming cap 400 can include features similar to those described with reference to other embodiments disclosed herein. As such, a description of some similar features is not repeated herein for clarity and brevity.

The IV priming cap 400 includes a cover body 402 and a coupling tab 404. The cover body 402 includes a proximal end 406 and a distal end 408, opposite the proximal end 406. An inner surface 410 of the cover body 402 defines a cavity, which extends into the cover body 402 and is configured to receive a fluid connector therein. A longitudinal connector cavity axis 4A extends between the proximal end 406 and the distal end 408 of the cover body 402.

The coupling tab 404 of the IV priming cap 400 extends away from the cover body 402 in a direction that is transverse relative to the connector cavity axis 4A. The coupling tab includes a base portion coupled to the cover body 402 and a tip portion distal to the cover body 402.

The base portion of the coupling tab 404 extends along the outer surface of the cover body 402 over an angle 4C around the connector cavity axis 2A. In some embodiments of the present disclosure, the angle 4C is at least about 10 degrees and/or less than or equal to about 90 degrees. In some embodiments, the base portion extends along the outer surface of the cover body 402 over an angle of about 90 degrees around the connector cavity axis 4A.

The base portion extends from the cover body 402 a first direction, and the tip portion extends from the base portion in a second direction, which is different than the first direction. The first direction is transverse to the connector cavity axis 4A and extends away from the outer surface of the cover body 402. The second direction is also transverse to the connector cavity axis 4A, but extends toward the outer surface of the cover body 402. Together, the base portion and the tip portion form a hook-shaped coupling tab 404 having an inner surface forming a tubing passage 446 with a longitudinal tubing passage axis 4B therethrough. The tubing passage axis 4B is parallel relative to the longitudinal connector cavity axis 4A. In some embodiments, the tubing passage axis 4B extends at an angle that is transverse relative to the connector cavity axis 4A.

In some embodiments, the tubing passage 446 has a diameter that is less than a diameter of the IV line so that the coupling tab 404 engages against the IV line and resists movement between IV priming cap 400 and the IV line.

At least a portion of a slot 448 can be formed between the coupling tab 404 and the cover body 402. More specifically, the slot 448 can be formed between the tip portion of the coupling tab 404 and an outer surface of the cover body 402. The slot 448 extends between the tubing passage 446 and the outer surface of the coupling tab 404. In some embodiments, the slot 448 is oriented to extend, between the tubing passage 446 and the outer surface of the coupling tab 404, in a direction toward the base portion of the coupling tab 404.

The coupling tab 404 is shaped as a wall having a height and a width. The height of the coupling tab 404 extends between a proximal surface, facing toward the direction of the proximal end 406, and a distal surface, facing toward the direction of the distal end 408. Along the base portion of the coupling tab 404, the width decreases away from the cover body 402. In some embodiments, the width increases toward the cover body 402 along the tip portion of the coupling tab 404.

The distal surface comprises a recessed surface 450 so that at least a portion of the perimeter of the coupling tab 404 comprises a wall 452 that extends above the recessed surface 450. In some embodiments of the present disclosure, any of the proximal surface and the distal surface of coupling tab 404 can include a recessed surface. The recessed surface 450 and wall 452 provide structural rigidity while reducing the amount of material necessary to form the coupling tab 404.

The tubing passage 446 and slot 448 permit a length of IV line to be moved into the tubing passage 446. When a length of IV line is inserted through the slot 448 to the tubing passage 446, the rigidity of the coupling tab 404, relative to the IV line, resists deformation or urging of the coupling tab 404. Where the tubing passage 446 has a cross-sectional length that is less than a diameter of the IV line, the length of IV line inserted into the tubing passage 446 is compressed.

The tubing passage 446 and slot 448 can also permit the IV priming cap 400 to be coupled with another structure, such as a pole or clamp. When the coupling tab 404 is coupled with a length of IV line, the length of IV line will extend generally aligned along the longitudinal tubing passage axis 4B, and the distal end portion of the IV line will be generally aligned along the longitudinal connector cavity axis 4A.

In some embodiments of the present disclosure, the IV priming cap 500 includes a clip-shaped coupling tab 504, as illustrated in FIGS. 7A-7D.

The IV priming cap 500 can include features similar to those described with reference to other embodiments disclosed herein. As such, a description of some similar features is not repeated herein for clarity and brevity.

The IV priming cap 500 includes a cover body 502 and a coupling tab 504. The cover body 502 includes a proximal end 506 and a distal end 508, opposite the proximal end 506. The cover body 502 includes an inner surface 510 defining a cavity extending into the cover body 502 and configured to receive a fluid connector therein. A longitudinal connector cavity axis 5A extends between the proximal end 506 and the distal end 508 of the cover body 502.

The coupling tab 504 of the IV priming cap 500 extends away from the cover body 502 in a direction that is transverse relative to the connector cavity axis 5A. The coupling tab includes a base portion 562 coupled to the cover body 502, a middle portion 564 extending from the base portion and distal to the cover body 502, and a tip portion 566 extending from the middle portion.

The base portion 562 extends from the cover body 502 in a first direction, which is transverse to the connector cavity axis 5A and extends away from the outer surface of the cover body 502. The middle portion 564 extends from the base portion 562 in a second direction, which is different than the first direction. The tip portion 566 extends from the middle portion 564 in a third direction, which is different than the first and second direction. In some embodiments, the third direction is also transverse to the connector cavity axis 5A, but extends toward the outer surface of the cover body 502.

The base portion 562, the middle portion 564, and the tip portion 566 form a clip-shaped coupling tab 504 having an inner surface forming a tubing passage 546 with a longitudinal tubing passage axis 5B therethrough.

The second direction can be any of parallel and transverse to the connector cavity axis 5A. In embodiments where the second direction is parallel to the connector cavity axis 5A, the tubing passage axis 5B is transverse to the connector cavity axis 5A. In embodiments where the second direction is transverse to the connector cavity axis 5A, the tubing passage axis 5B is parallel to the connector cavity axis 5A.

A distance between the outer surface of the cover body 502 and the inner surface of the middle portion 564 is less than a diameter of the IV line so that the coupling tab 500 engages against the IV line and resists movement between IV priming cap 500 and the IV line.

At least a portion of a slot 548 can be formed between the coupling tab 504 and the cover body 502. More specifically, the slot 548 can be formed between the tip portion of the coupling tab 504 and an outer surface of the cover body 502. The slot 548 extends between the tubing passage 546 and the outer surface of the coupling tab 504. The slot 548 is oriented to extend, between the tubing passage 546 and the outer surface of the coupling tab 504, in a direction toward the base portion of the coupling tab 504.

The coupling tab 504 is shaped as a wall having a height, a width, and a length. The height of the coupling tab 504 extends between a proximal surface, facing toward the direction of the proximal end 506, and a distal surface, facing toward the direction of the distal end 508. The length of the coupling tab 504 is a direction from the base portion 562 to the tip portion 566, and the width of the coupling tab 504 is a direction transverse to the length of the coupling tab 504.

Any of the base portion 562, the middle portion 564, and the tip portion 566, can have a height that decreases along of a length of the respective portion. The base portion 562 can have a height H10, and the tip portion 566 can have a height H12, which is less than the height H10. Between the base portion 562 and the tip portion 566, the middle portion 564 comprises a height that decreases from the height H10 to the height H12.

The width of the coupling tab 504 is less than the height H10 and the height H12. The width of the coupling tab 504 and the reduced height of the tip portion 566, relative to the base portion 562 provides a coupling tab 504 that is more flexible in an area adjacent the tip portion 566, relative to an area adjacent the base portion 562. The flexibility of the tip portion 566 can permit the tip portion 566 to be flexible and moved away from the cover body 502, while the less flexible base portion 562, relative to the tip portion 566, resists damage to the IV priming cap 500 when the coupling tab 504 is coupled to an IV line or other structure.

The tall height of the coupling tab 504, relative to the width, provides a large inner surface area of the coupling tab 504 to engage against the length of IV line is inserted into the tubing passage 548. Engagement of the inner surface of the coupling tab 504 resists sliding or movement of the IV line relative to the IV priming cap 500.

The length L10 of the coupling tab 504 is less than the cross-sectional length L12 of the cover body 502 adjacent the proximal end 506. The length L10 of the coupling tab 504 is approximately equal to the height H10 of the base portion 562. Because the length L10 of the coupling tab 504 is approximately equal to the height H10 of the base portion 562, the coupling tab 504 is less flexible, in a direction toward or away from the cover body 502, relative to a coupling tab 504 having a length that is greater than length L10.

A tip portion of the coupling tab 504 can include a protrusion 560 having outer surfaces that extend away from the outer surfaces of the coupling tab 504. The protrusion 560 can be cylindrically shaped and extend longitudinally along the height of the coupling tab 504. In some embodiments, the protrusion 560 can comprise a cross-sectional shape that includes any of a circle, an ellipse, a semicircle, and a polygon. In some embodiments, a cross-sectional profile of the protrusion 560, transverse to the tubing passage axis 5B, comprises a width that tapers along the height of the coupling tab 504.

The tubing passage 546 and slot 548 permit a length of IV line to be moved into the tubing passage 546. The tubing passage 546 and slot 548 can also permit the IV priming cap 500 to be coupled with another structure, such as a pole or clamp. When the coupling tab 504 is coupled with a length of IV line, the length of IV line will extend generally aligned along the longitudinal tubing passage axis 5B, and the distal end portion of the IV line will be generally aligned along the longitudinal connector cavity axis 5A.

In some embodiments of the present disclosure, an IV priming cap 500 includes an elongated clip-shaped coupling tab 504, as illustrated in FIGS. 8A-8D. The elongated coupling tab 504 includes a long length relative to the height of the coupling tab 504.

The base portion 562 has a height H10, and the tip portion 566 can have a height H14, which is less than the height H10 and height H12. Between the base portion 562 and the tip portion 566, the middle portion 564 comprises a height that decreases from the height H10 toward the height H14. In some embodiments, the height H10 of the base portion 562 is less than the height H14 of the tip portion 566, and a height of the middle portion 564 can increase from the height H10 toward the height H14.

The length L14 of the elongated coupling tab 504 is approximately equal to the cross-sectional length L12 of the cover body 502 adjacent the proximal end 506. The length L14 of the coupling tab 504 is greater than the height H10 of the base portion 562. In some embodiments, the length L14 of the coupling tab 504 twice as long as the height H10 of the base portion 562.

Because the length L14 of the elongated coupling tab 504 is greater than the height H10 of the base portion 562, the elongated coupling tab 504 is more flexible, in a direction toward or away from the cover body 502, relative to a coupling tab 504 having a length that is less than or equal to the height H10

Because the elongated coupling tab 504 is more flexible, a length of IV line positioned between the cover body 502 and the elongated coupling tab 504 may not be compressed, thereby permitting unobstructed flow through the IV line. Additionally, the elongated coupling tab 504 can be used to couple the IV priming cap to other structures, such a railing.

Referring to FIGS. 9A-9D, another embodiment of an IV priming cap 600 having a clip-shaped coupling tab 604 is illustrated. The IV priming cap 600 can include features similar to those described with reference to other embodiments disclosed herein. As such, a description of some similar features is not repeated herein for clarity and brevity.

The IV priming cap 600 includes a cover body 602 and a coupling tab 604. The cover body 602 includes a proximal end 606 and a distal end 608, opposite the proximal end 606. An inner surface 610 of the cover body 602 defines a cavity, which extends into the cover body 602 and is configured to receive a fluid connector therein. A longitudinal connector cavity axis 6A extends between the proximal end 606 and the distal end 608 of the cover body 602.

The coupling tab 604 of the IV priming cap 600 extends away from the cover body 602 in a direction that is transverse relative to the connector cavity axis 6A. The coupling tab includes a base portion 662 coupled to the cover body 602 and a tip portion 666 that extends from the base portion 662. The base portion 662 extends from the cover body 602 a first direction, and the tip portion 666 extends from the base portion 662 in a second direction, which is different than the first direction.

The coupling tab 604 includes a side surface extending along the base portion 662 and the tip portion 666. At least a portion of the side surface of the base portion 662 and the side surface of the tip portion 666 face opposite to each other and are spaced apart to form a tubing passage 646.

The tubing passage 646 extends through the coupling tab 604, between a proximal surface, facing toward the direction of the proximal end 606, and a distal surface, facing toward the direction of the distal end 608. The tubing passage 646 is oriented through the coupling tab 604 to form a longitudinal tubing passage axis 6B that is parallel relative to the longitudinal connector cavity axis 6A. In some embodiments, the tubing passage axis 6B extends at an angle that is transverse relative to the connector cavity axis 6A. Additionally, the side surfaces of the base portion 662 and the tip portion 666 form a slot 648. The slot 648 extends between the tubing passage 646 and the outer surface of the coupling tab 604.

The side surfaces side surfaces of the base portion 662 and the tip portion 666 that form the slot 648 and the tubing passage 646 can extends generally parallel to each other, taper toward each other, and taper away from each other.

Figure 9A:
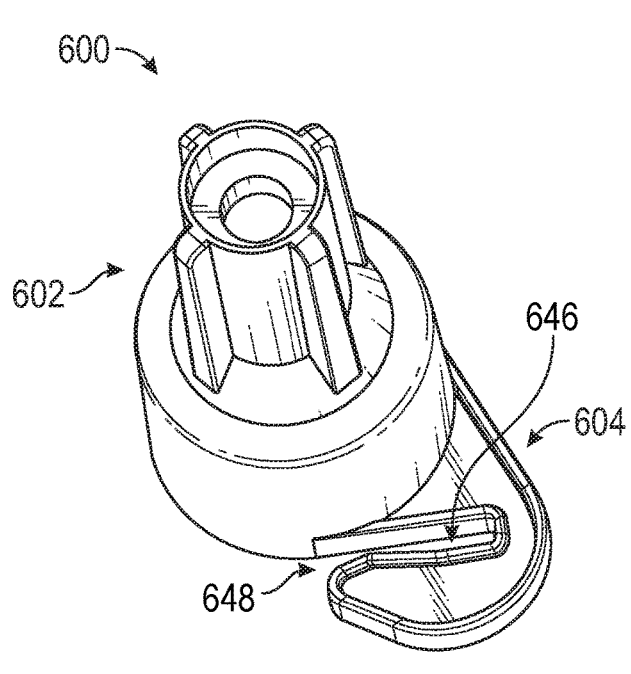
FIG. 9A is a top perspective view of another embodiment of an IV priming cap, according to some embodiments.
Figure 9B:
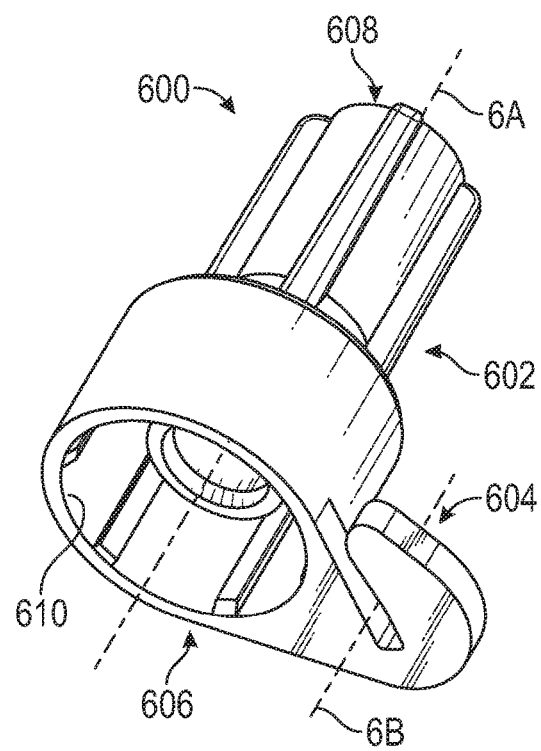
FIG. 9B is a bottom perspective view of the IV priming cap of FIG. 9A.
Figure 9C:
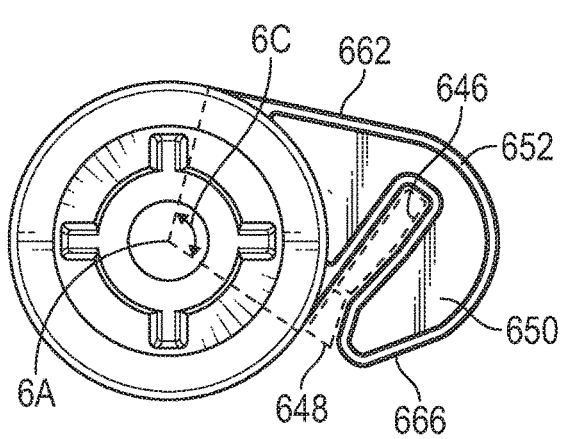
FIG. 9C is a top view of the IV priming cap of FIG. 9A.
Figure 9D:
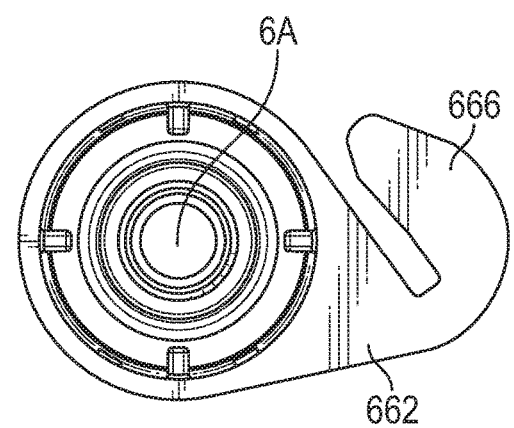
FIG. 9D is a bottom view of the IV priming cap of FIG. 9A.
Figure 10A:
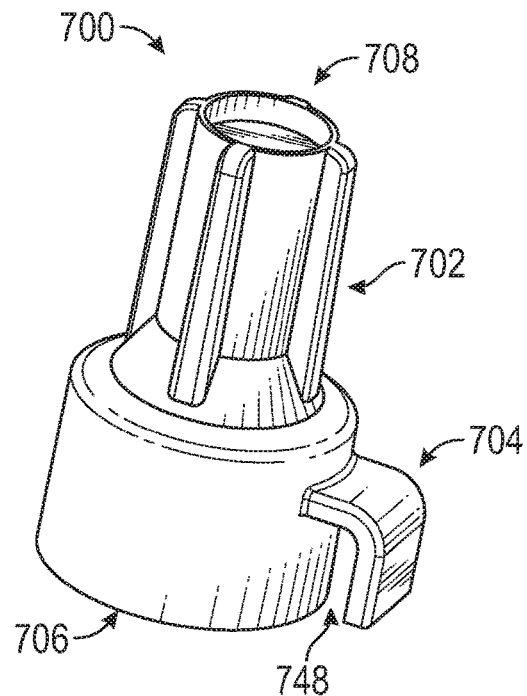
FIG. 10A is a top perspective view of another embodiment of an IV priming cap, according to some embodiments.
Figure 10B:
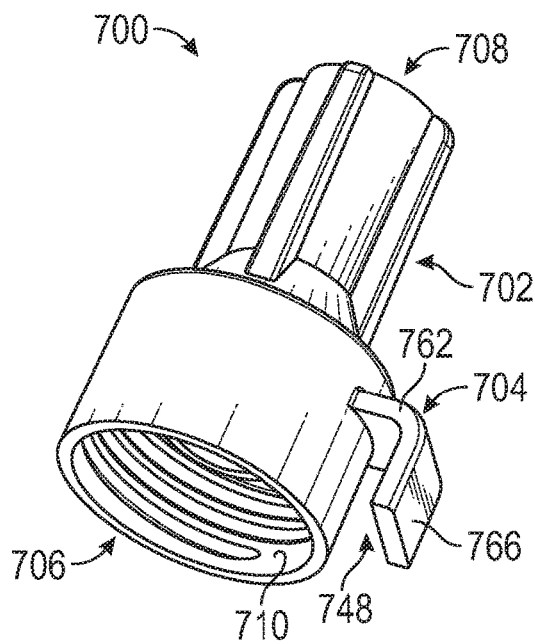
FIG. 10B is a bottom perspective view of the IV priming cap of FIG. 10A.
Figure 10C:
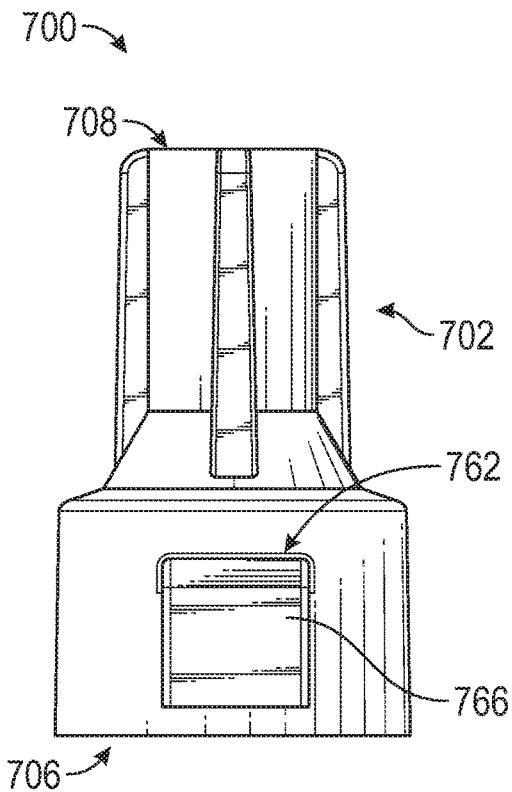
FIG. 10C is a front view of the IV priming cap of FIG. 10A.
Figure 10D:
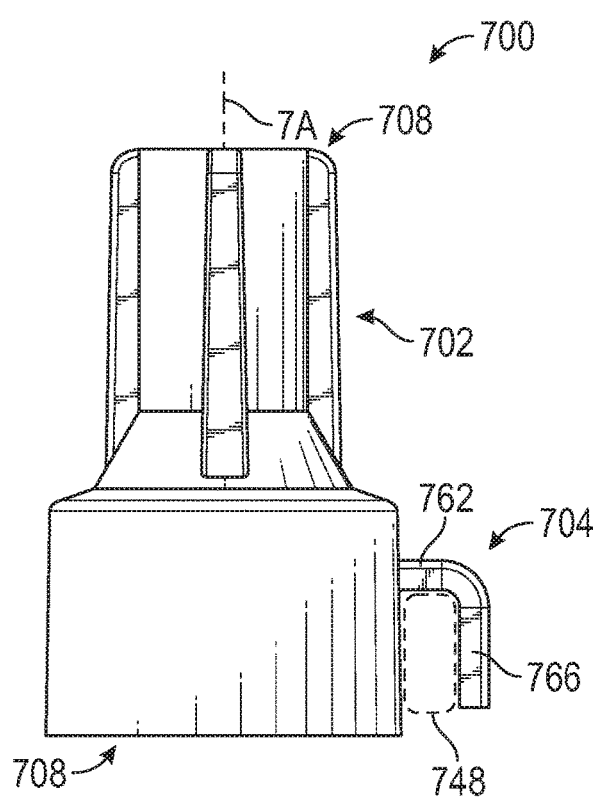
FIG. 10D is a side view of the IV priming cap of FIG. 10A.

Referring to FIG. 9C, the width between the side surfaces of the base portion 662 and the tip portion 666 can decrease along a first length to form a tapered slot 648. The width between the side surfaces then increases from the slot 648 to the tubing passage 646.

The width between side surfaces side surfaces of the coupling tab 604 that form the tubing passage 646 and the slot 648 can be less than a diameter of the IV line so that length of IV line is compressed when moved into the tubing passage 648.

The distal surface comprises a recessed surface 650 so that at least a portion of the perimeter of the coupling tab 604 comprises a wall 652 that extends above the recessed surface 650. In some embodiments of the present disclosure, any of the proximal surface and the distal surface of coupling tab 604 can include a recessed surface. The recessed surface 650 and wall 652 provide structural rigidity while reducing the amount of material necessary to form the coupling tab 604.

The base portion 662 extends along the outer surface of the cover body 602 over an angle 6C around the connector cavity axis 6C. In some embodiments, the base portion extends along the outer surface of the cover body 602 over an angle of about 90 degrees around the connector cavity axis 6A.

The tubing passage 646 and slot 648 permit a length of IV line to be moved into the tubing passage 646. When a length of IV line is inserted through the slot 648 to the tubing passage 646, the rigidity of the coupling tab 604, relative to the IV line, resists deformation or moving of the coupling tab 604.

Figure 12:
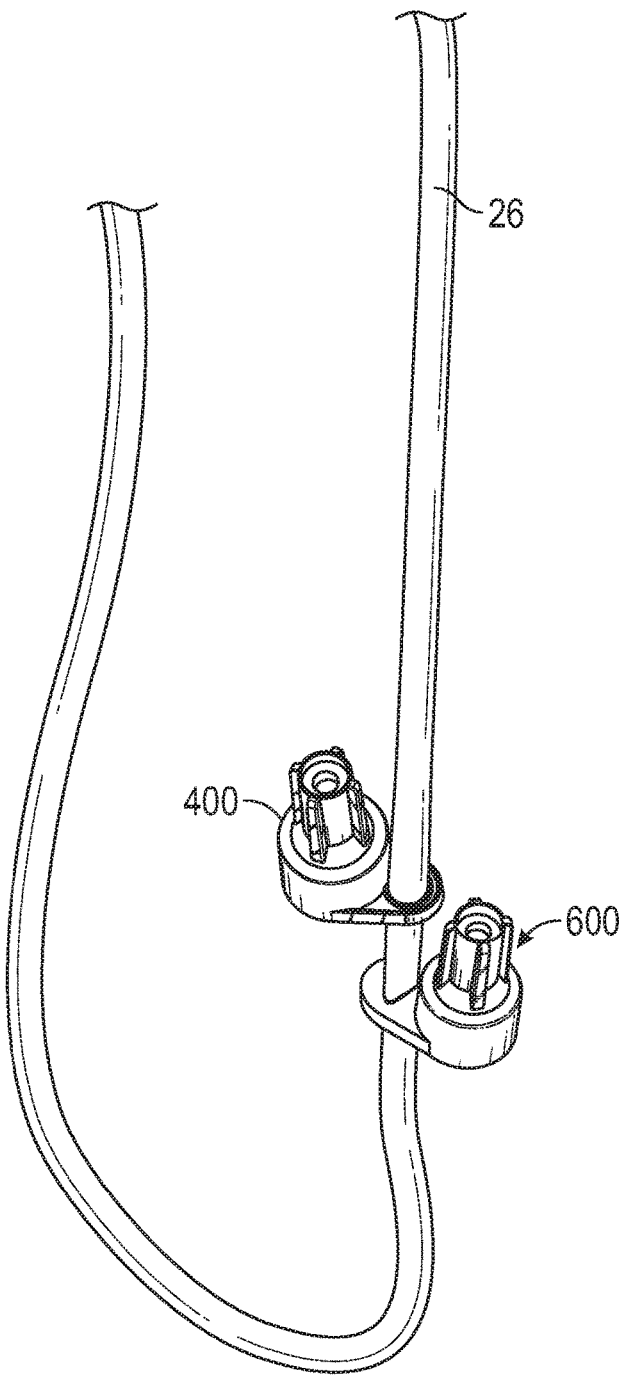

In use, a length of IV line is compressed as it is moved along the narrowing portion of the slot 648 and into the tubing passage 646 of the IV priming cap 600 (FIG. 12). The cross-sectional width of the tubing passage 646 can be configured to completely or partially occlude the fluid passage through the IV line.

Referring to FIGS. 10A-10D, another embodiment of an IV priming cap 700 having a hook-shaped coupling tab 704 is illustrated. The IV priming cap 400 can include features similar to those described with reference to other embodiments disclosed herein. As such, a description of some similar features is not repeated herein for clarity and brevity.

The IV priming cap 700 includes a cover body 702 and a coupling tab 704. The cover body 702 includes a proximal end 706 and a distal end 708, opposite the proximal end 706. An inner surface 710 of the cover body 702 defines a cavity, which extends into the cover body 702 and is configured to receive a fluid connector therein. A longitudinal connector cavity axis 7A extends between the proximal end 706 and the distal end 708 of the cover body 702.

The coupling tab 704 of the IV priming cap 700 extends away from the cover body 702 in a direction that is transverse relative to the connector cavity axis 7A. The coupling tab includes a base portion 762 coupled to the cover body 702 and a tip portion 766 distal to the cover body 702.

The base portion 762 extends from the cover body 702 a first direction, and the tip portion 766 extends from the base portion 762 in a second direction, which is different than the first direction.

The first direction is transverse to the connector cavity axis 7A so that the base portion 762 extends away from the outer surface of the cover body 702. The second direction is different than the first direction so that the tip portion 766 extends along the outer surface of the cover body 702. In some embodiments, the second direction is parallel relative to the connector cavity axis 7A. In some embodiments, the second direction is any angle that is transverse relative to the first direction.

The tip portion 766 is spaced apart from the cover body 702 forming a slot 748 between an outer surface of the cover body 702 and inner surfaces of the base portion 762 and the tip portion 766.

The slot 748 extends between the cover body 702 and the tip portion 766, in a direction from the base portion 762 toward the proximal end 706 of the cover body 702. Additionally, the slot 748 extends laterally, relative to the connector cavity axis 7A.

Figure 11:
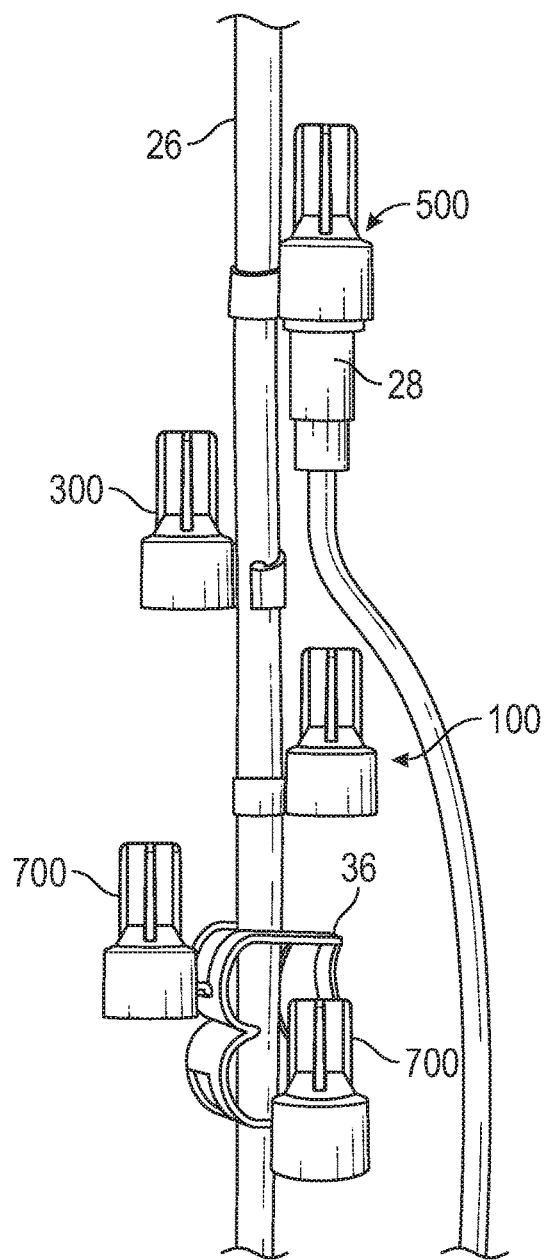
FIGS. 11 and 12 are perspective views of IV priming caps, according to some embodiments, coupled to portions of an IV administration set.

In use, the IV priming cap 700 can be coupled to a structure, such as a roller clamp 30 (FIG. 2) or a pinch clamp 36 (FIG. 11). For example, referring to FIGS. 10D and 11, the IV priming cap 700 is coupled to the pinch clamp 36 by moving the IV priming cap 700 toward the pinch clamp 36 until the coupling tab 704 engages a portion of the pinch clamp 36 in the slot 748.

In some embodiments, a distance between the outer surface of the cover body 702 and the inner surfaces of the tip portion 766 is less than an outer surface diameter of an IV line. The IV priming cap 700 can be coupled to the IV line by moving a length of the IV line into the slot 748 of the coupling tab 704.

In some embodiments of the present disclosure, the IV priming cap can include more than one coupling tab. For example, an IV priming cap can include a first coupling tab and a second coupling tab, wherein the first and second coupling tabs have features disclosed with reference to coupling tabs any of coupling tabs 104, 204, 304, 404, 504, 604, and 704. In some embodiments, an IV priming cap includes a first coupling tab 704 and a second coupling tab 104. In other embodiments, an IV priming cap includes a first coupling tab 604 and a second coupling tab 104.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. An intravenous (IV) priming cap comprising: a cover body having a proximal end, a distal end, and an inner surface defining a connector cavity extending into the cover body from the proximal end toward the distal end, wherein the connector cavity comprises a longitudinal connector cavity axis extending from the proximal end toward the distal end of the cover body; a priming passage the extends from within the connector cavity to outside the cover body; and a coupling tab extending from an outer surface of the cover body, the coupling tab comprising a base portion coupled to the cover body, a tip portion distal to the cover body, a tubing passage through the coupling tab, and a slot extending through an outer surface of the coupling tab to the tubing passage, wherein the coupling tab is configured to engage against a length of tubing moved through the slot to the tubing passage.

Clause 2. The IV priming cap of Clause 1, wherein the coupling tab comprises a first coupling arm and a second coupling arm, each of the first coupling arm and the second coupling arm extending between the base portion and the tip portion of the coupling tab.

Clause 3. The IV priming cap of Clause 2, wherein each of the first coupling arm and the second coupling arm comprise an inner surface facing the other of the first coupling arm and the second coupling arm, and wherein the tubing passage and the slot are defined between the inner surface of the first coupling arm and the second coupling arm.

Clause 4. The IV priming cap of Clause 1, wherein the slot extends in a direction from the tip portion of the coupling tab toward the base portion.

Clause 5. The IV priming cap of Clause 1, wherein the coupling tab comprises an inner surface defining the tubing passage and the slot between the inner surface of the coupling tab and the outer surface of the cover body.

Clause 6. The IV priming cap of Clause 5, wherein the coupling tab extends along the outer surface of the cover body in a direction that is transverse to the longitudinal connector cavity axis.

Clause 7. The IV priming cap of Clause 1, wherein the base portion extends from the cover body in a first direction transverse to the longitudinal connector cavity axis, and the tip portion extends from the base portion in a second direction that is different than the first direction.

Clause 8. The IV priming cap of Clause 7, wherein the second direction is transverse to the longitudinal connector cavity axis.

Clause 9. The IV priming cap of Clause 1, wherein the cover body comprises any of a rib and channel extending along the outer surface of the cover body.

Clause 10. The IV priming cap of Clause 1, wherein the priming passage extends through any of the proximal end and the distal end of the cover body.

Clause 11. The IV priming cap of Clause 1, comprising a hydrophobic filter positioned along the priming passage.

Clause 12. An intravenous (IV) priming cap comprising: a cover body having a proximal end, a distal end, and an inner surface defining a connector cavity extending into the cover body, wherein the connector cavity comprises a longitudinal connector cavity axis between the proximal end and the distal end, and a priming passage extends from within the connector cavity to outside the cover body; and a coupling tab extending from an outer surface of the cover body, the coupling tab comprising a base portion coupled to the cover body, a tip portion distal to the cover body, and a slot defined between an inner surface of the coupling tab and the outer surface of the cover body.

Clause 13. The IV priming cap of Clause 12, wherein the slot extends in a direction from the proximal end toward the distal end of the cover body.

Clause 14. The IV priming cap of Clause 12, wherein the slot extends laterally, relative to the longitudinal connector cavity axis.

Clause 15. The IV priming cap of Clause 12, wherein the base portion extends from the cover body in a first direction transverse to the longitudinal connector cavity axis, and the tip portion extends from the base portion in a second direction that is different than the first direction.

Clause 16. The IV priming cap of Clause 15, wherein the second direction is transverse to the longitudinal connector cavity axis.

Clause 17. The IV priming cap of Clause 12, wherein the cover body comprises any of a rib and channel extending along the outer surface of the cover body.

Clause 18. The IV priming cap of Clause 12, wherein the priming passage extends through any of the proximal end and the distal end of the cover body.

Clause 19. The IV priming cap of Clause 12, comprising a hydrophobic filter positioned along the priming passage.

Clause 20. An intravenous (IV) administration set comprising: IV line comprising a distal end, a fluid connector configured to couple with the distal end of the IV line, and an IV priming cap configured to couple with the fluid connector, the IV priming cap comprising: a cover body having a proximal end, a distal end, and an inner surface defining a connector cavity extending into the cover body, and a priming passage the extends from within the connector cavity to outside the cover body; and a coupling tab extending from an outer surface of the cover body, the coupling tab comprising a base portion coupled to the cover body, a tip portion distal to the cover body, and a slot defined between an inner surface of the coupling tab and the outer surface of the cover body, wherein the coupling tab is configured to engage a length of IV line positioned through the slot.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

In one or more aspects, the terms "about," "substantially," and "approximately" may provide an industry-accepted tolerance for their corresponding terms and/or relativity between items.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

What is claimed is:

1. An intravenous (IV) priming cap comprising:
a cover body having a proximal end, a distal end, and an inner surface defining a connector cavity extending into the cover body from the proximal end toward the distal end, the connector cavity comprising a first end at the proximal end of the cover body and a second end proximal to the distal end of the cover body and defining a distalmost end of the connector cavity, wherein a cross-sectional width of the connector cavity tapers from the first end of the connector cavity to the second end of the connector cavity, and wherein the connector cavity comprises a longitudinal connector cavity axis extending from the proximal end toward the distal end of the cover body;
a priming passage that extends from the second end of the connector cavity to outside the cover body, the priming passage comprising a volume that is less than a volume of the connector cavity; and
a coupling tab extending from an outer surface of the cover body, the coupling tab comprising a base portion coupled to the cover body, a middle portion extending from the base portion, and a tip portion, wherein the tip portion extends from the middle portion toward the cover body, and wherein the coupling tab comprises a height extending from a proximal surface of the coupling tab to a distal surface of the coupling tab, and in a first direction from the proximal end toward the distal end of the cover body, wherein the proximal surface of the coupling tab extends from the base portion to the tip portion, wherein the proximal end of the cover body and the proximal surface of the coupling tab are coplanar, and the distal surface along the middle portion of the coupling tab extends in a direction toward the proximal surface such that the height of the coupling tab decreases from the base portion toward the tip portion of the coupling tab, and
a tubing passage through the coupling tab, and a slot extending through an outer surface of the coupling tab to the tubing passage, wherein the tubing passage extends entirely through the coupling tab in the first direction to define a longitudinal tubing passage axis such that the coupling tab is configured to engage against a length of tubing moved through the slot to the tubing passage.

2. The IV priming cap of claim 1, wherein the coupling tab comprises a first coupling arm and a second coupling arm, each of the first coupling arm and the second coupling arm extending between the base portion and the tip portion of the coupling tab.

3. The IV priming cap of claim 2, wherein each of the first coupling arm and the second coupling arm comprise an inner surface facing the other of the first coupling arm and the second coupling arm, and wherein the tubing passage and the slot are defined between the inner surface of the first coupling arm and the second coupling arm.

4. The IV priming cap of claim 1, wherein the slot extends in a direction from the tip portion of the coupling tab toward the base portion.

5. The IV priming cap of claim 1, wherein the coupling tab comprises an inner surface, and wherein the tubing passage and the slot are formed between the inner surface of the coupling tab and the outer surface of the cover body.

6. The IV priming cap of claim 5, wherein the coupling tab extends along the outer surface of the cover body in a second direction that is transverse to the longitudinal connector cavity axis.

7. The IV priming cap of claim 1, wherein the base portion extends from the cover body in a second direction that is transverse to the longitudinal connector cavity axis, and the tip portion extends from the base portion in a third direction that is different than the second direction.

8. The IV priming cap of claim 7, wherein the third direction is transverse to the longitudinal connector cavity axis.

9. The IV priming cap of claim 1, wherein the cover body comprises any of a rib and channel extending along the outer surface of the cover body.

10. The IV priming cap of claim 1, wherein the priming passage extends through any of the proximal end and the distal end of the cover body.

11. The IV priming cap of claim 1, comprising a hydrophobic filter positioned along the priming passage.

12. The IV priming cap of claim 1, wherein the coupling tab comprises a length, defined from the base portion to the tip portion, that is approximately equal to a cross-sectional length defined by the outer surface of the cover body at the proximal end thereof.

13. An intravenous (IV) priming cap comprising: a cover body having a proximal end, a distal end, and an inner surface defining a connector cavity extending into the cover body, the connector cavity comprising a cross-sectional width that tapers from a first end of the connector cavity at the proximal end of the cover body to a second end of the connector cavity adjacent to the distal end of the cover body and defining a distalmost end of the connector cavity, and wherein the connector cavity comprises a longitudinal connector cavity axis between the proximal end and the distal end, and a priming passage extends from within the connector cavity to outside the cover body, the priming passage comprising a volume that is less than a volume of the connector cavity; and a coupling tab extending from an outer surface of the cover body, the coupling tab comprising a base portion coupled to the cover body, a middle portion extending from the base portion, and a tip portion, a tubing passage, and a slot defined between an inner surface of the coupling tab and the outer surface of the cover body, wherein the tip portion extends from the middle portion toward the cover body, the coupling tab comprises a height extending in a first direction from a proximal surface of the coupling tab to a distal surface of the coupling tab, wherein the proximal surface of the coupling tab extends from the base portion to the tip portion, wherein the proximal end of the cover body and the proximal surface of the coupling tab are coplanar, and the distal surface along the middle portion of the coupling tab extends in a direction toward the proximal surface such that the height of the coupling tab decreases from the base portion toward the tip portion of the coupling tab, and wherein the tubing passage and the slot extend entirely through the coupling tab, in the first direction.

14. The IV priming cap of claim 13, wherein the slot extends laterally, relative to the longitudinal connector cavity axis.

15. The IV priming cap of claim 13, wherein the base portion extends from the cover body in a second direction that is transverse to the longitudinal connector cavity axis, and the tip portion extends from the base portion in a third direction that is different than the second direction.

16. The IV priming cap of claim 15, wherein the third direction is transverse to the longitudinal connector cavity axis.

17. The IV priming cap of claim 13, wherein the cover body comprises any of a rib and channel extending along the outer surface of the cover body.

18. The IV priming cap of claim 13, wherein the priming passage extends through any of the proximal end and the distal end of the cover body.

19. The IV priming cap of claim 13, comprising a hydrophobic filter positioned along the priming passage.

20. The IV priming cap of claim 13, wherein the coupling tab comprises a width extending in a second direction, where the second direction is transverse relative to the first direction, and wherein the width of the coupling tab decreases from the base portion toward the tip portion of the coupling tab.

21. An intravenous (IV) administration set comprising:

an IV line comprising a distal end and an outer surface defining a diameter of the IV line, a fluid connector configured to couple with the distal end of the IV line, and an IV priming cap configured to couple with the fluid connector, the IV priming cap comprising:

a cover body having a proximal end, a distal end, and an inner surface defining a connector cavity extending into the cover body, and a priming passage that extends from a second end of the connector cavity to outside the cover body, the connector cavity comprising a cross-sectional width that tapers from a first end of the connector cavity at the proximal end of the cover body to the second end of the connector cavity adjacent to the distal end of the cover body, the second end defining a distalmost end of the connector cavity, and the priming passage comprising a volume that is less than a volume of the connector cavity; and a coupling tab extending from an outer surface of the cover body, the coupling tab comprising a base portion coupled to the cover body, a middle portion extending from the base portion, and a tip portion, a tubing passage defined by an inner surface of the coupling tab, and a slot extending between the inner surface of the coupling tab and the outer surface of the cover body, wherein the tip portion extends from the middle portion toward the cover body, the coupling tab comprises a height extending in a first direction from a proximal surface of the coupling tab to a distal surface of the coupling tab, wherein the proximal surface of the coupling tab extends from the base portion to the tip portion, wherein the proximal end of the cover body and the proximal surface of the coupling tab are coplanar, and the distal surface along the middle portion of the coupling tab extends in a direction toward the proximal surface such that the height of the coupling tab decreases from the base portion toward the tip portion of the coupling tab, and wherein the tubing passage and the slot extend entirely through the coupling tab in the first direction, and a width of the slot is less than the diameter of the IV line such that the inner surface of the coupling tab is configured to engage against and compress a length of IV line positioned through the slot.

* * * * *